US010456452B2

(12) United States Patent
Ghoroghchian et al.

(10) Patent No.: US 10,456,452 B2
(45) Date of Patent: Oct. 29, 2019

(54) COMPOSITIONS AND METHODS FOR IMPROVED ENCAPSULATION OF FUNCTIONAL PROTEINS IN POLYMERIC VESICLES

(71) Applicant: POSEIDA THERAPEUTICS, INC., San Diego, CA (US)

(72) Inventors: P. Peter Ghoroghchian, Boston, MA (US); Jivan Namdeo Yewle, Lexington, KY (US)

(73) Assignee: Poseida Therapeutics, Inc., San Diego, CA (US)

(*) Notice: Subject to any disclaimer, the term of this patent is extended or adjusted under 35 U.S.C. 154(b) by 78 days.

(21) Appl. No.: 15/198,836

(22) Filed: Jun. 30, 2016

(65) Prior Publication Data

US 2017/0000734 A1 Jan. 5, 2017

Related U.S. Application Data

(60) Provisional application No. 62/187,942, filed on Jul. 2, 2015.

(51) Int. Cl.
*A61K 38/42* (2006.01)
*A61K 9/10* (2006.01)
*A61K 9/127* (2006.01)

(52) U.S. Cl.
CPC ............... *A61K 38/42* (2013.01); *A61K 9/10* (2013.01); *A61K 9/1273* (2013.01)

(58) Field of Classification Search
None
See application file for complete search history.

(56) References Cited

U.S. PATENT DOCUMENTS

| | | |
|---|---|---|
| 5,227,170 A | 7/1993 | Sullivan |
| 5,256,422 A | 10/1993 | Albert et al. |
| 5,595,756 A | 1/1997 | Bally et al. |
| 5,612,310 A | 3/1997 | Dewhirst et al. |
| 5,833,974 A | 11/1998 | Teicher |
| 6,133,316 A | 10/2000 | Østensen et al. |
| 6,835,394 B1 | 12/2004 | Discher et al. |
| 7,217,427 B2 | 5/2007 | Discher et al. |
| 7,417,118 B2 | 8/2008 | Kai et al. |
| 7,867,512 B2 | 1/2011 | Discher et al. |
| 7,998,458 B2 | 8/2011 | Sung et al. |
| 8,808,748 B2 | 8/2014 | Ghoroghchian et al. |
| 9,421,247 B2 | 8/2016 | Ghoroghchian et al. |
| 9,533,027 B2 | 1/2017 | Ghoroghchian et al. |
| 2003/0162693 A1 | 8/2003 | Winslow et al. |
| 2003/0180365 A1 | 9/2003 | Barnikol |
| 2004/0265835 A1 | 12/2004 | Lemaster et al. |
| 2005/0019265 A1 | 1/2005 | Hammer et al. |
| 2005/0129747 A1 | 6/2005 | Barnikol et al. |
| 2005/0287145 A1 | 12/2005 | Stewart et al. |
| 2005/0287189 A1 | 12/2005 | Noujaim et al. |
| 2006/0249456 A1 | 11/2006 | Fukutomi et al. |
| 2008/0102128 A1 | 5/2008 | Constancis et al. |
| 2010/0203149 A1 | 8/2010 | Radosz et al. |
| 2010/0255112 A1 | 10/2010 | Discher et al. |
| 2010/0311168 A1 | 12/2010 | Samuel et al. |
| 2010/0331819 A1 | 12/2010 | Hossainy et al. |
| 2011/0059157 A1 | 3/2011 | Awasthi et al. |
| 2011/0223128 A1 | 9/2011 | Grutzendler et al. |
| 2012/0144618 A1 | 5/2012 | Nolta et al. |
| 2013/0177641 A1 | 7/2013 | Ghoroghchian |
| 2013/0202559 A1 | 8/2013 | Skog et al. |
| 2014/0255477 A1 | 9/2014 | Ghoroghchian |
| 2014/0315985 A1 | 10/2014 | May et al. |
| 2014/0363496 A1 | 12/2014 | Ghoroghchian |
| 2015/0232881 A1 | 8/2015 | Glucksmann et al. |
| 2017/0000743 A1 | 1/2017 | Ghoroghchian et al. |
| 2017/0105929 A1 | 4/2017 | Ghoroghchian et al. |

(Continued)

FOREIGN PATENT DOCUMENTS

| | | |
|---|---|---|
| WO | WO 00/02580 A2 | 1/2000 |
| WO | WO 03/059363 A1 | 7/2003 |
| WO | WO 2009/002274 A1 | 12/2008 |

(Continued)

OTHER PUBLICATIONS

Kishimura et al. "Encapsulation of Myoglobin in PEGylated Polyion Complex Vesicles made from a pair of oppositely charged block ionomers: a physiologically available oxygen carrier" Angew Chem Int Ed 46: 6085-6088 (2007) (Year: 2007).*

C. Sanson et al.; Temperature Responsive poly(trimethylene carbonate)-block-poly(L-glutamic acid) copolymer: polymersomes fusion and fission; Nov. 24, 2009; www.rsc.org/softmatter; The Royal Society of Chemistry 2010.

Shahid Rameez et al.; Large Scale Production of Vesicles by Hollow Fiber Extrusion: A Novel Method for Generating Polymersome Encapsulated Hemoglobin Dispersions; Langmuir Article; pubs.acs.org/Langmuir; William G. Lowrie Department of Chemical and Biomolecular Engineering, The Ohio State University, 425 Koffolt Laboratories, 140 West 19th Avenue, Columbus, Ohio 43210.

Wei Qi et al.; Aqueous self-assembly of poly(ethylene oxide)-block-poly(e-caprolacone)(PEO-b-PCL) copolymers: disaparate diblock coplymer compositions give rise to nano- and mes-scale bilayered vesicles; Nanoscale RSC Publishing; The Royal Society of Chemistry 2013; www.rsc.org/nanoscale; published Sep. 5, 2013.

(Continued)

*Primary Examiner* — Anand U Desai
(74) *Attorney, Agent, or Firm* — Cooley LLP; Ivor R. Elrifi; Matthew Pavao

(57) ABSTRACT

Methods of preparing polymersome-encapsulated functional protein suspensions may include thermally blending an amount of a block copolymer with an amount of a low molecular weight polyethylene glycol (PEG) for at least 30 minutes, mixing and cooling a resulting PEG/polymer formulation to room temperature, adding an aliquot of a solution of the functional protein to a sample containing the PEG/polymer formulation, and performing at least three dilution steps in which polymersomes that are generated are progressively saturated with the functional protein. The aliquot of the solution of the functional protein added may have a to the PEG/polymer sample of around 0.5:1 to 1.5:1 by volume, and the thermal blending may be performed at 90-100° C.

11 Claims, 13 Drawing Sheets

(56) References Cited

U.S. PATENT DOCUMENTS

2017/0360706 A1 12/2017 Ghoroghchian
2017/0361126 A1 12/2017 Ghoroghchian

FOREIGN PATENT DOCUMENTS

| WO | WO 2010/118077 A1 | 10/2010 |
|---|---|---|
| WO | WO 2011/133635 A2 | 10/2011 |
| WO | WO 2012/094679 A2 | 7/2012 |
| WO | WO 2014/021408 A1 | 2/2014 |
| WO | WO 2015/089462 A1 | 6/2015 |
| WO | WO 2015/191693 A2 | 12/2015 |
| WO | WO 2016/090111 A1 | 6/2016 |
| WO | WO 2017/004509 A1 | 1/2017 |

OTHER PUBLICATIONS

Peter J. Photos et al.; Polymer Vesicles in vivio: correlations with PEG molecular weight; Journal of Controlled Release; Elsevier B. V.; www.elsevier.com/locate/jconrel; Journal of Controlled Release 2003.

Gautam D. Pangu et al.; Ultrasonically Induced Release from Nanosized Polymer Vesicles; Macromolecular Bioscience; Macromolecular Journals; Wiley-VCH Verlag GmbH & Co. KGaA, Weinheim 2010.

Dalia Hope Levine et al.; Polymersomes: A new multi-functional Tool for Cancer Diagnosis and Therapy; Elsevier Methods; journal www.elsevier.com/locate/ymeth; Methods 46, 2008.

James C-M. Lee et al.; Preparation, Stability, and In Vitro Performance of Vesicles Made with Diblock Copolymers; John Wiley & Sons, Inc. 2001.

P. Peter Ghoroghchian et al.; Near-Infrared-Emissive Polymersomes: Self-Assembled Soft Matter for in vivo optical Imaging; PNAS www.pnas.org/cgi/doi/10.1073/pnas.0409394102; vol. 102, No. 8; Feb. 22, 2005.

P. Peter Ghoroghchian et al.; Controlling Bulk Optical Properties of Emissive Polymersomes Through Intramembranous Polymer-Fluorophore Interations; NIH Public Access Author Manuscript; Chem Mater. 19(6): 1309-1318; doi: 10.1021/cm062427w; Mar. 20, 2007.

Bohdana M. Discher et al.; Polymersomes: Tough Vesicles Made from Diblock Copolymers; Science vol. 284, 1143 doi: 10.1126/science.284.25417.1143; www.sciencemag.org; May 14, 1999.

Natalie A. Christian et al.; Tat-Functionalized Near-Infrared Emissive Polymersomes for Dendritic Cell Labeling; Bioconjugate Chem vol. 18 pp. 31-40; American Chemical Society; Nov. 22, 2006.

Shahid Ramez et al.; Biocompatible and Biodegradable Polymersome Encapsulated Hemoglobin: A Potential Oxygen Carrier; Bioconjugate Chem vol. 19 pp. 1025-1032; American Chemical Society; Apr. 29, 2008.

Dian R. Arifin et al.; Polymersome Encapsulated Hemoglobin: A Novel Type of Oxygen Carrier; Biomacromolecules vol. 6 pp. 2172-2181; American Chemical Society; Jun. 4, 2005.

Interntaiontal Search Report and Written Opinion for International Application No. PCT/US2016/040657 dated Oct. 13, 2016.

O'Neil, C. P. et al., A novel method for the encapsulation of biomolecules into polymersomes via direct hydration, Langmuir, 2009, vol. 25, No. 16, pp. 9025-9029.

Sui, X. et al., Robust formation of biodegradable polymersomes by direct hydration, Polymer Chemistry, 2015 (E-pub. Nov. 18, 2014), vol. 6, pp. 691-696.

Qiao, Z.-Y. et al., Polymersomes from dual responsive block copolymers: Drug encapsulation by heating and acid-triggered release, Biomacromolecules, 2013, vol. 14, pp. 1555-1563.

Lee, J. S. et al., Polymersomes for drug delivery: design, formation and characterization, Journal of Controlled Release, 2012, vol. 161, pp. 473-483.

Yewle, J. et al., Progressive saturation improves the encapsulation of functional proteins in nanoscale polymer vesicles, Pharmaceutical Research, 2016 (E-pub. Oct. 27, 2015), vol. 33, pp. 573-589.

Canton, I. et al. "Fully Synthetic Polymer Vesicles for Intracellular Delivery of Antibodies in Live Cells", *The FASEB Journal*, p. 1-11, 2012.

Egli, S. et al., "Functionalization of block copolymer vesicle surfaces", *Polymers*, vol. 3, Issue 1, p. 252-280, 2011.

Kim, Younghoon, et al. "Polymersome Delivery of siRNA and Antisense Oligonucleotides", *Journal of Controlled Release at ScienceDirect*, p. 132-140, 2009.

Lee, J. S. "Biodegradable polymersomes for drug delivery" *Enschede*, 166p PhD thesis, 172 pages, 2011.

Levine, D. et al. "Polymersomes: A New Mutli-Functional Tool for Cancer Diagnosis and Therapy", *Methods*, vol. 46, No. 1, p. 25-32, 2008.

Li, S. et al. "Self-Assembled Poly(butadiene)-b-Poly(ethylene oxide) Polymersomes as Paclitaxel Carriers" *Biotechnol Prog.*, vol. 23, No. 1, p. 278-285, 2007.

Liaw J. et al. "In Vivo gene Delivery into Ocular Tissues by Eye Drapes of poly(ethylene oxide)-poly(propylene oxide)-poly(ethylene oxide) (PEO-PPO-PEO) polymeric micelles" *Gene Therapy*, vol. 8, p. 999-1004, 2001.

Meng, F. et al. "Intracellular drug release nanosystems", *Materials Today*, vol. 15, Issue 10, p. 436-442, 2012.

Onaca, O. et al. "Stimuli-Responseive Polymersomes as Nanocarriers for Drug and Gene Delivery", *Macromolecular Bioscience*, vol. 9, p. 129-139, 2009.

Yin, H. et al. "Therapeutic Genome Editing by Combined Viral and Non-Viral Delivery of CRISPR System Components in Vivo" *Nature Biotechnology Letters*, vol. 34, No. 3, p. 328-333, 2016.

Arifin, D.R. and A.F. Palmer (2005) "Polymersome Encapsulated Hemoglobin: A Novel Type of Oxygen Carrier" *Biomacromolecules*, 6:2172-2181.

Cai, Y. et al. (Apr. 2014) "Targeted genome editing by lentiviral protein transduction of zinc-finger and TAL-effector nucleases" *ELIFE*, 3:e01911; DOI: 10.7554/eLife.01911; 19 pages.

Chang, T.M.S. (2006) "Blood substitutes based on nanobiotechnology" *Trends in Biotechnology*, vol. 24, No. 8, p. 372-377.

Csaba et al. "Preparation of Poly(Lactic Acid) (PLA) and Poly(Ethylene Oxide) (PEO) Nanoparticles as Carriers for Gene Delivery" Cold Spring Harb Protocols. vol. 2010, Issue 8, August, pp. 1-4.

De Wilt, J.H.W. et al. (2000) "Nitric oxide synthase inhibition results in synergistic anti-tumour activity with melphalan and tumour necrosis factor alpha-based isolated limb perfusions" *Br J Cancer*, 83(9):1176-1182.

Discher, B.M. et al. (May 14, 1999) "Polymersomes: Tough Vesicles Made from Diblock Copolymers" *Science*, 284:1142-1146.

Hammadi, A. et al. (2008) "Stimulation of iNOS expression and apoptosis resistance in B-cell chronic lymphocytic leukemia (B-CLL) cells through engagement of Toll-like Receptor 7 (TLR-7) and NF-kappaB activation" *Nitric Oxide*, vol. 19, p. 138-145.

Hong, W. et al. (2013) "Reversing multidrug resistance by intracellular delivery of Pluronic® P85 unimers" *Biomaterials*, 34:9602-9614.

Hong, W. et al. (2017) "pH-sensitive micelles for the intracellular co-delivery of curcumin and Pluronic L61 unimers for synergistic reversal effect of multidrug resistance" *Scientific Reports*, 7:42465; DOI: 10.1038/srep42465, 20 pages.

Hu, J. et al. (2013) "pH-responsive and charge shielded cationic micelle of poly(L-histidine)-block-short branched PEI for acidic cancer treatment" *J Control Rel*, 172:69-76.

Jeffs et al. (Mar. 2005) "A Scalable, Extrusion-Free Method for Efficient Liposomal Encapsulation of Plasmid DNA" *Pharmaceutical Research*, vol. 22, No. 3, p. 362-372.

Kamga, C. et al. (2012) "Myoglobin and mitochondria: A relationship bound by oxygen and nitric oxide" *Nitric Oxide*, 26:251-258.

Lee, E.S. et al. (2007) "Tumor pH-responsive flower-like micelles of poly(L-lactic acid)-b-poly(ethylene glycol)-b-poly(L-histidine)" *J Control Rel*, 123:19-26.

Liang, X. et al. (2015) "Rapid and highly efficient mammalian cell engineering via Cas9 protein transfection" *J Biotechnol*, 208:44-53.

Liu, Z. and N. Zhang (2012) "pH-Sensitive Polymeric Micelles for Programmable Drug and Gene Delivery" *Curr Pharmaceut Des*, 18:3442-3451.

(56) References Cited

OTHER PUBLICATIONS

Mikkelsen, J.G. et al. (Oct. 2003) "Helper-Independent *Sleeping Beauty* Transposon-Transposase Vectors for Efficient Nonviral Gene Delivery and Persistent Gene Expression in Vivo" *Molecular Therapy*, vol. 8, No. 4, p. 654-665.

Oh, K.T. et al. (2008) "L-Histidine-based pH-sensitive anticancer drug carrier micelle: Reconstitution and brief evaluation of its sytemic toxicity" *Int J Pharmaceut*, 358:177-183.

Özcan, I. et al. (2010) "Pegylation of poly(γ-benzyl-L-glutamate) nanoparticles is efficient for avoiding mononuclear phagocyte system capture in rats" *Intl J Nanomedicine*, 5:1103-1111.

Piras, A. et al. (2008) "Polymeric nanoparticles for hemoglobin-based oxygen carriers" *Biochimica et Biophysica Acta*, 1784:1454-1461.

Watanabe, K.I. et al. (2000) "Nitric oxide synthase inhibitor suppresses the ototoxic side effect of cisplatin in guinea pigs" *Anti-cancer Drugs*, vol. 11(5) (Abstract). Obtained from //www.ncbi.nlm.nih.gov/pubmed/10912957 on Jul. 9, 2018, 1 pg.

Wei, Q. et al. (2013) "Aqueous self-assembly of poly(ethylene ozide)-block-poly(ε-caprolactone) (PEO-b-PCL) copolymers: disparate diblock copoymer compositions give rise to nano- and meso-scale bilayered vesicles" *Nanoscale*, 5:10908-10915.

Xu, Feng et al. (2009) "Long-circulation of hemoglobin-loaded polymeric nanoparticles as oxygen carriers with modulated surface charges" *International Journal of Pharmaceuticals*, vol. 377, p. 199-206.

Zhang, H-H. et al. (2008) "Y-Shaped Poly(ethylene glycol) and Poly(trimethylene carbonate) Amphiphilic Copolymer: Synthesis and for Drug Delivery" *J Polymer Sci: Part A: Polymer Chem*, 46:8131-8140.

Zhang, X. et al. (2014) "Poly(L-histidine) Based Triblock Copolymers: pH Induced Reassembly of Copolymer Micelles and Mechanism Underlying Endolysosomal Escape for Intracellular Delivery" *Biomacromolecules*, 15:4032-4045.

Zupancich, J.A. et al. (2006) "Aqueous Dispersions of Poly(ethylene oxide)-b-poly (γ-methyl-ε-caprolactone) Block Copolymers" *Macromolecules*, 39:4286-4288.

Adelstein, D.J. et al. (1997) "A Phase III Randomized Trial Comparing Concurrent Chemotherapy and Radiotherapy with Radiotherapy Alone in Resectable Stage III and IV Squamous Cell Head and Neck Cancer: Preliminary Results" *Head and Neck*, 19:567-575.

Ahmed, F. et al. (2006) "Biodegradable Polymersomes Loaded with Both Paclitaxel and Doxorubicin Permeate and Shrink Tumors, Inducing Apoptosis in Proportion to Accumulated Drug" *J Control Release*, 116:150-158.

Ahn, G.O. et al. (2007) "Targeting Tumors with Hypoxia-Activated Cytotoxins" *Frontiers in Bioscience*, 12:3483-3501.

Alarćon, R. et al. (Dec. 1999) "Hypoxia Induces p53 Accumulation through MDM2 Down-Regulation and Inhibition of E6-Mediated Degradation" *Cancer Research*, 59:6046-6054.

Alayash, A.I. (2014) "Blood Substitutes: Why Haven't We Been More Successful?" *Trends Biotechnol*, 32:177-185.

Alberts et al., *Molecular Biology of the Cell*, 3rd ed. New York: Garland Publishing, Inc., 1994; pp. 489-493; pp. 800-801.

American Cancer Society (2010) *Cancer Facts and Figures 2010* [online]. Retrieved from: www.cancer.org/research/cancerfactsfigures/cancerfactsfigures/cancer-facts-and-figures-2010; retreived on Oct. 10, 2011, 62 pages.

Angelova, M.I. et al. (1992) "Preparation of giant vesicles by external AC electric fields. Kinetics and applications" *Prog Coll Polym Sci*, 89:127-131.

Ansari, A. et al. (1994) "Conformational Relaxation and Ligand-Binding in Myoglobin" *Biochemistry*, 33:5128-5145.

Aquino-Parsons, C. et al. (1999) "Carbogen Inhalation in Cervical Cancer: Assessment of Oxygenation Change" *Gynecologic Oncology*, 74:259-264.

Aranda-Espinoza, H. et al. (Nov. 2001) "Electromechanical Limits of Polymersomes" *Physical Review Letters* 87(20):208301_1-4.

Ather, M.H. and T.S. Masood (2010) "Current management of advanced and metastatic renal cell carcinoma" *Urology Journal*, 7:1-9.

Bache, M. et al. (2008) "Detection and Specific Targeting of Hypoxic Regions within Solid Tumors: Current Preclinical and Clinical Strategies" *Current Medicinal Chemistry*, 15:322-338.

Bates, F.S. (Feb. 22, 1991) "Polymer-Polymer Phase Behavior" *Science*, 251(4996):898-905.

Benjamini, Y. and Y. Hochberg (1995) "Controlling the false discovery rate: A practical and powerful approach to multiple testing" *Journal of the Royal Statistical Society. Series B (Methodological)*, 57:289-300.

Bermúdez, H. et al. (2002) "Molecular Weight Dependence of Polymersome Membrane Structure, Elasticity, and Stability" *Macromolecules*, 35:8203-8208.

Bermúdez, H. et al. (2004) "Effect of Bilayer Thickness on Membrane Bending Rigidity" *Langmuir*, 20:540-543.

Bernier, J. et al. (2000) "ARCON: Accelerated Radiotherapy with Carbogen and Nicotinamide in Head and Neck Squamous Cell Carcinomas. The Experience of the Cooperative Group of Radiotherapy of the European Organization for Research and Treatment of Cancer (EORTC)", *Radiotherapy and Oncology*, 55:111-119.

Binder, W.H. et al. (2007) "Guiding the Location of Nanoparticles Into Vesicular Structures: A Morphological Study" *Physical Chemistry Chemical Physics*, 9:6435-6441.

Blanazs, A. et al. (2009) "Tailoring Macromolecular Expression at Polymersome Surfaces" *Advanced Functional Materials*, 19:2906-2914.

Bloom, M. et al. (1991) "Physical properties of the fluid lipid-bilayer component of cell membranes: a perspective" *Q Rev Biophys*, 24(3):293-397.

Brahmer, J.R. et al. (2012) "Safety and Activity of Anti-PD-LI Antibody in Patients with Advanced Cancer" *New England Journal of Medicine*, 366:2455-2465.

Brizel, D.M. et al. (1997) "Tumor Hypoxia Adversely Affects the Prognosis of Carcinoma of the Head and Neck" *International Journal of Radiation Oncology Biology Physics*, 38:285-289.

Brizel, D.M. et al. (1999) "Oxygenation of Head and Neck Cancer: Changes During Radiotherapy and Impact on Treatment Outcome" *Radiotherapy and Oncology*, 53:113-117.

Bromley, E.H.C. et al. (2008) "Peptide and Protein Building Blocks for Synthetic Biology: From Programming Biomolecules to Self-Organized Biomolecular Systems" *ACS Chemical Biology*, 3:38-50.

Brown, J.M. (1999) "The Hypoxic Cell: A Target for Selective Cancer Therapy—Eighteenth Bruce F. Cain Memorial Award Lecture" *Cancer Research*, 59:5863-5870.

Brown, J.M. and L-H. Wang (1998) "Tirapazamine: Laboratory Data Relevant to Clinical Activity" *Anti-Cancer Drug Design*, 13:529-539.

Bunn, H.F. (1995) "The Role of Hemoglobin Based Substitutes in Transfusion Medicine" *Transfus Clin Biol*, 2:433-439.

Bussink, J. et al. (1999) "Clinical Outcome and Tumour Microenvironmental Effects of Accelerated Radiotherapy with Carbogen and Nicotinamide" *Acta Oncologica*, 38:875-882.

Cabrales, P. (2013) "Examining and mitigating acellular hemoglobin vasoactivity" *Antioxid Redox Signal*, 18:2329-2341.

Cabrales, P. and J.M. Friedman (2013) "HBOC vasoactivity: interplay between nitric oxide scavenging and capacity to generate bioactive nitric oxide species" *Antioxid Redox Signal*, 18:2284-2297.

Carlson, D.J. et al. (2009) "Towards Temporal Optimization of Radiation Fractionation: The Kinetic Effects of Tumor Hypoxia, DNA Damage Repair, and Tumor Cell Repopulation" *International Journal of Radiation Oncology Biology Physics*, 75:S615-S616; Abstract 1968.

Castillo, R.V. et al. (2010) "Crystallization Kinetics and Morphology of Biodegradable Double Crystalline PLLA-b-PCL Diblock Copolymers" *Macromolecules*, 43:4149-4160.

Chaieb, S. and Rica, S. (Dec. 1998) "Spontaneous curvature-induced pearling instability" *Phys Rev E*, 58(6):7733-7737.

Chance, B. (1991) "Optical Method" *Annual Review of Biophysics and Biophysical Chemistry*, 20:1-28.

(56) References Cited

OTHER PUBLICATIONS

Chance, B. et al. (1988) "Time-Resolved Spectroscopy of Hemoglobin and Myoglobin in Resting and Ischemic Muscle" *Analytical Biochemistry*, 174:698-707.
Chang, A. et al. (Jan. 2014) "Chronic Kidney Disease in Patients with Renal Cell Carcinoma" *Advances in Chronic Kidney Disease*, 21:91-95.
Chang, T.M.S. (2010) "Blood replacement with nanobiotechnologically engineered hemoglobin and hemoglobin nanocapsules" *Wiley Interdisciplinary Reviews: Nanomedicine and Nanobiotechnology*, 2:418-430.
Chang, Y. et al. (2007) "Sorafenib (BAY 43/9006) inhibits tumor growth and vascularization and induces tumor apoptosis and hypoxia in RCC xenograft models" *Cancer Chemother Pharmacol*, 59:561-574.
Chen, J.Y. et al. (2009) "A Review of Blood Substitutes: Examining the History, Clinical Trial Results, and Ethics of Hemoglobin-Based Oxygen Carriers" *Clinics*, 64:803-813.
Chen, W. et al. (2010) "pH-Sensitive Degradable Polymersomes for Triggered Release of Anticancer Drugs: A Comparative Study with Micelles" *J Control Release*, 142:40-46.
Chin, A.I. et al. (2006) "Surveillance Strategies for Renal Cell Carcinoma Patients Following Nephrectomy" *Reviews in Urology*, 8:1-7.
Cho, D. et al. (2007) "The role of mammalian target of rapamycin inhibitors in the treatment of advanced renal cancer" *Clin Cancer Res*, 13:758s-763s.
Cho, D.C. et al. (2010) "The Efficacy of the Novel Dual PI3-Kinase/mTOR Inhibitor NVP-BEZ235 Compared with Rapamycin in Renal Cell Carcinoma" *Clinical Cancer Research*, 16:3628-3638.
Choueiri, T.K. (Mar. 2008) "Factors associated with outcome in patients with advanced renal cell carcinoma in the era of antiangiogenic agents" *Clin Genitourin Cancer*, 6:15-20.
Choueiri, T.K. (2012) "Efficacy of cabozantinib (XL184) in patients (pts) with metastatic, refractory renal cell carcinoma (RCC)" 2012 ASCO Annual Meeting. *J Clin Oncol*, 30(Suppl):Abstract 4504 [online]. Retrieved from: meeting.library.asco.org/content/95382-114; retrieved on May 4, 2017, 2 pages.
Choueiri, T.K. et al. (2007) "Clinical factors associated with outcome in patients with metastatic clear-cell renal cell carcinoma treated with vascular endothelial growth factor-targeted therapy" *Cancer*, 110:543-550.
Choueiri, T.K. et al. (2007) "Prognostic factors associated with long-term survival in previously untreated metastatic renal cell carcinoma" *Ann Oncol*, 18:249-255.
Christian, D.A. et al. (2009) "Polymersome Carriers: From Self-Assembly to siRNA and Protein Therapeutics" *Eur J Pharm Biopharm*, 71:463-474.
Christian, D.A. et al. (2010) "Polymer Vesicles with a Red Cell-like Surface Charge: Microvascular Imaging and in vivo Tracking with Near-Infrared Fluorescence" *Macromolecular Rapid Communications*, 31:135-141.
Christian, N.A. et al. (2009) "In Vivo Dendritic Cell Tracking Using Fluorescence Lifetime Imaging and Near-Infrared-Emissive Polymersomes" *Mol Imaging Biol*, 11:167-177.
Clifford, S.C. and E.R. Maher (2001) "von Hippel-Lindau disease: clinical and molecular perspectives" *Adv Cancer Res*, 82:85-105.
Conley, K.E. and Jones, C. (1996) "Myoglobin Content and Oxygen Diffusion: Model Analysis of Horse and Steer Muscle" American Journal of Physiology, *Cell Physiology*, 271:C2027-C2036.
Conover, C.D. et al. (Mar. 1999) "The ability of polyethylene glycol conjugated bovine hemoglobin (PEG-Hb) to adequately deliver oxygen in both exchange transfusion and top-loaded rat models" *Artif Cells Blood Substit Immobil Biotechnol*, 27(2):93-107.
Cornelissen, J.J.L.M. et al. (May 29, 1998) "Helical Superstructures from Charged Poly(styrene)-Poly(isocyanodipeptide) Block Copolymers" *Science*, 280:1427-1430.
Courtney, K.D. and T.K. Choueiri (2009) "Optimizing recent advances in metastatic renal cell carcinoma" *Curr Oncol Rep*, 11:218-226.

Courtney, K.D. and T.K. Choueiri (2010) "Updates on novel therapies for metastatic renal cell carcinoma" *Therapeutic Advances in Medical Oncology*, 2:209-219.
Craighead, P.S. et al. (2000) "A Phase I/II Evaluation of Tirapazamine Administered Intravenously Concurrent with Cisplatin and Radiotherapy in Women with Locally Advanced Cervical Cancer" *International Journal of Radiation Oncology Biology Physics*, 48:791-795.
Cristofanilli, M. et al. (Jun. 2002) "Angiogenesis modulation in cancer research: novel clinical approaches" *Nature Reviews Drug Discovery*, 1:415-426.
De La Fouchardiere, C. et al. (2010) "Phase I Study of Daily Irinotecan As a Radiation Sensitizer for Locally Advanced Pancreatic Cancer" *International Journal of Radiation Oncology Biology Physics*, 77:409-413.
Deuling, H.J. and W. Helfrich (Nov. 1976) "The Curvature Elasticity of Fluid Membranes: A Catalogue of Vesicle Shapes" *J Phys*, 37:1335-1345.
Dewhirst, M.W. (2009) "Relationships Between Cycling Hypoxia, HIF-1, Angiogenesis and Oxidative Stress" *Radiation Research*, 172:653-665.
Dewhirst, M.W. et al. (1996) "Microvascular Studies on the Origins of Perfusion-Limited Hypoxia" *British Journal of Cancer*, 74:S247-S251.
Dewhirst, M.W. et al. (2007) "Exploring the Role of HIF-1 in Early Angiogenesis and Response to Radiotherapy" *Radiotherapy and Oncology*, 83:249-255.
Dewhirst, M.W. et al. (2008) "Cycling Hypoxia and Free Radicals Regulate Angiogenesis and Radiotherapy Response" *Nature Reviews Cancer*, 8:425-437.
Dewhirst, M.W. et al. (2010) "Utility of Functional Imaging in Prediction or Assessment of Treatment Response and Prognosis Following Thermotherapy" *International Journal of Hyperthermia*, 26:283-293.
Dietz, A. et al. (1999) "Rise of Oxygenation in Cervical Lymph Node Metastasis During the Initial Course of Radiochemotherapy" *Otolaryngology Head and Neck Surgery*, 121:789-796.
Ding, J. and Lieu, G. (1998) "Water-Soluble Hollow Nanospheres as Potential Drug Carriers" *J Phys Chem B*, 102:6107-6113.
Discher, B.M. et al. (2000) "Polymer Vesicles in Various Media" *Curr Opin Colloid Interface Sci*, 5:125-131.
Discher, D.E. et al. (2007) "Emerging Applications of Polymersomes in Delivery: From Molecular Dynamics to Shrinkage of Tumors" *Prog Polym Sci*, 32:838-857.
Döbereiner, H.-G. et al. (Apr. 1997) "Mapping vesicle shapes into the phase diagram: A comparison of experiment and theory" *Phys Rev E*, 55:4458-4474.
Dobrowsky, W. (1992) "Mitomycin-C, 5-Fluorouracil and Radiation in Advanced, Locally Recurrent Rectal Cancer" *British Journal of Radiology*, 65:143-147.
Doehn, C. et al. (2009) "Mode-of-Action, Efficacy, and Safety of a Homologous Multi-Epitope Vaccine in a Murine Model for Adjuvant Treatment of Renal Cell Carcinoma" *European Urology*, 56:123-131.
Duncan, T.V. et al. (2008) "Ultrafast Excited-State Dynamics of Nanoscale Near-Infrared Emissive Polymersomes" *J Am Chem Soc*, 130:9773-9784.
Dusenbery, K.E. et al. (1994) "Erythropoietin Increases Hemoglobin During Radiation Therapy for Cervical Cancer" *International Journal of Radiation Oncology Biology Physics*, 29:1079-1084.
Eisbruch, A. et al. (1999) "Bromodeoxyuridine Alternating with Radiation for Advanced Uterine Cervix Cancer: A Phase I and Drug Incorporation Study" *Journal of Clinical Oncology*, 17:31-40.
English Translation of WO 2014/021408 A1. Obtained from https://patents.google.com/patent/WO2014021408A1/en?oq=nmma+and+paclitaxel on Jul. 9, 2018. Originally published in Japanese on Feb. 6, 2014. 29 printed pages.
Escudier, B. et al. (2014) "Randomized, Controlled, Double-Blind, Cross-Over Trial Assessing Treatment Preference for Pazopanib Versus Sunitinib in Patients with Metastatic Renal Cell Carcinoma: PISCES Study" Journal of Clinical Oncology, 32:1412-1418.

(56) References Cited

OTHER PUBLICATIONS

Evans, E. and Needham, D. (1987) "Physical Properties of Surfactant Bilayer Membranes: Thermal Transitions, Elasticity, Rigidity, Cohesion, and Colloidal Interactions" *J Phys Chem*, 91:4219-4228.

Evans, E. and Rawicz, W. (Apr. 23, 1990) "Entropy-Driven Tension and Bending Elasticity in Condensed-Fluid Membranes" *Phys Rev Lett* 64(17):2094-2097.

Evans, S.M. et al. (1997) "Evaluation of the Concept of "Hypoxic Fraction" as a Descriptor of Tumor Oxygenation Status" *Oxygen Transport to Tissue XVIII. Adv Exp Med Biol*, 411:215-225.

Feldman, D.R. et al. (2009) "Phase I Trial of Bevacizumab Plus Escalated Doses of Sunitinib in Patients with Metastatic Renal Cell Carcinoma" *Journal of Clinical Oncology*, 27:1432-1439.

Feldmann, H.J. et al. (1999) "Blood flow and oxygenation status of human tumors. Clinical investigations" *Strahlentherapie Und Onkologie*, 175:1-9.

Fendler, J.H. (Mar. 2, 1984) "Polymerized Surfactant Vesicles: Novel Membrane Mimetic Systems" *Science*, 223(4639):888-894.

Fenton, B.M. et al. (2000) "Enhancement of Tumor Perfusion and Oxygenation by Carbogen and Nicotinamide During Single- and Multifraction Irradiation" *Radiation Research*, 153:75-83.

Figlin, R.A. et al. (May 2008) "Overall survival with sunitinib versus interferon (IFN)-alfa as first-line treatment of metastatic renal cell carcinoma (mRCC)" *Journal of Clinical Oncology*, 26(15 suppl):Abstract 5024 [online]. Retrieved from: http://ascopubs.org/doi/10.1200/jco.2008.26.15_suppl5024; retrieved on May 4, 2017, 2 pages.

Flögel, U. et al. (Apr. 2009) "Myoglobin Tames Tumor Growth and Spread" *Journal of Clinical Investigation*, 119:766-768.

Fogh, S. et al. (2010) "Phase I Trial Using Patupilone (Epothilone B) and Concurrent Radiotherapy for Central Nervous System Malignancies" *International Journal of Radiation Oncology Biology Physics*, 77:1009-1016.

Fontanella, A.N. et al. (2013) "Quantitative Mapping of Hemodynamics in the Lung, Brain, and Dorsal Window Chamber-Grown Tumors Using a Novel, Automated Algorithm" *Microcirculation*, 20:724-735.

Frauenfelder, H. et al. (Jul. 22, 2003) "Myoglobin: The Hydrogen Atom of Biology and a Paradigm of Complexity" *PNAS*, 100:8615-8617.

Fu, L. et al. (2011) "Generation of a Mouse Model of Von Hippel-Lindau Kidney Disease Leading to Renal Cancers by Expression of a Constitutively Active Mutant of HIF1alpha", *Cancer Research*, 71:6848-6856.

Fyles, A.W. et al. (1998) "Oxygenation Predicts Radiation Response and Survival in Patients with Cervix Cancer" *Radiotherapy and Oncology*, 48:149-156.

Gali-Muhtasib, H. et al. (2004) "Quinoxaline 1,4-Dioxides Are Novel Angiogenesis Inhibitors That Potentiate Antitumor Effects of Ionizing Radiation" *International Journal of Oncology*, 24:1121-1131.

Galluzzo, M. et al. (Apr. 2009) "Prevention of hypoxia by myoglobin expression in human tumor cells promotes differentiation and inhibits metastasis" *J Clin Invest*, 119(4):865-875.

Gatzemeier, U. et al. (1998) "Tirapazamine-Cisplatin: The Synergy" *British Journal of Cancer*, 77:15-17.

Ghoroghchian, P.P. et al. (2005) "Broad Spectral Domain Fluorescence Wavelength Modulation of Visible and Near-Infrared Emissive Polymersomes" *J Am Chem Soc*, 127:15388-15390.

Ghoroghchian, P.P. et al. (2006) "Bioresorbable Vesicles Formed through Spontaneous Self-Assembly of Amphiphilic Poly(ethylene oxide)-Block-Polycaprolactone" *Macromolecules*, 39:1673-1675.

Ghoroghchian, P.P. et al. (2006) "Quantitative Membrane Loading of Polymer Vesicles" *Soft Matter*, 2:973-980.

Ghoroghchian, P.P. et al. (2009) "In Vivo Fluorescence Imaging: A Personal Perspective" *WIRE Nanomed Nanobiotechnol*, 1:156-167.

Golshayan, A.R. et al. (Jan. 2009) "Metastatic Sarcomatoid Renal Cell Carcinoma Treated with Vascular Endothelial Growth Factor-Targeted Therapy" Journal of Clinical Oncology, 27:235-241.

Gottschalk, A. et al. (2005) "Influence of the Hemoglobin Solution HBOC-201 on Tissue Oxygenation in the Rat R1H-Tumor" *Artif Cells Blood Substit Biotechnol*, 33:379-389.

Graeber, T.G. et al. (1996) "Hypoxia-Mediated Selection of Cells with Diminished Apoptotic Potential in Solid Tumors" Nature, 379:88-91.

Grepin, R. et al. (2012) "Acceleration of clear cell renal cell carcinoma growth in mice following bevacizumab/Avastin treatment: the role of CXCL cytokines" *Oncogene*, 31:1683-1694.

Grigsby, P.W. et al. (1999) "Irradiation with or without Misonidazole for Patients with Stages IIIB and IVA Carcinoma of the Cervix: Final Results of RTOG 80-05" International Journal of Radiation Oncology Biology Physics, 44:513-517.

Grisanzio, C. et al. (2011) "Orthotopic xenografts of RCC retain histological, immunophenotypic and genetic features of tumours in patients" *Journal of Pathology*, 225:212-221.

Gundersen, S.I. et al. (2008) "Hemoglobin-Based Oxygen Carrier Enhanced Tumor Oxygenation: A Novel Strategy for Cancer Therapy" *Biotechnol Prog*, 24:1353-1364.

Haffty, B.G. et al. (1997) "Chemotherapy as an Adjunct to Radiation in the Treatment of Squamous Cell Carcinoma of the Head and Neck: Results of the Yale Mitomycin Randomized Trials" *J Clin Oncol*, 15:268-276.

Hahn, J.S. et al. (1997) "Stroma-Free Human Hemoglobin A Decreases R3230Ac Rat Mammary Adenocarcinoma Blood Flow and Oxygen Partial Pressure" *Radiation Research*, 147:185-194.

Hai, C. (2012) "Systems Biology of HBOC-Induced Vasoconstriction" *Current Drug Discovery Technologies*, 9:204-211.

Hajduk, D.A. et al. (1998) "Complex Phase Behavior in Aqueous Solutions of Poly (ethylene oxide)-Poly(ethylethylene) Block Copolymers" *J Phys Chem B*, 102:4269-4276.

Harasym, T.O. et al. (1997) "Intratumor distribution of doxorubicin following i.v. administration of drug encapsulated in egg phosphatidylcholine/cholesterol liposomes" *Cancer Chemother Pharmacol*, 40:309-317.

Hardee, M.E. et al. (2009) "Novel Imaging Provides New Insights into Mechanisms of Oxygen Transport in Tumors" *Current Molecular Medicine*, 9:435-441.

Harrison, L. et al. (2004) "Hypoxia and Anemia: Factors in Decreased Sensitivity to Radiation Therapy and Chemotherapy?" *Oncologist*, 9(Suppl 5):31-40.

Harrison, L.B. et al. (1998) "A Prospective Phase II Trial of Concomitant Chemotherapy and Radiotherapy with Delayed Accelerated Fractionation in Unresectable Tumors of the Head and Neck" *Head Neck*, 20:497-503.

Harrison, L.B. et al. (2002) "Impact of Tumor Hypoxia and Anemia on Radiation Therapy Outcomes" *Oncologist*, 7:492-508.

Hay, M.P. et al. (2004) "DNA-Targeted 1,2,4-Benzotriazine 1,4-Dioxides: Potent Analogues of the Hypoxia-Selective Cytotoxin Tirapazamine" *Journal of Medicinal Chemistry*, 47:475-488.

Hearnden, V. et al. (Jul. 2009) "Diffusion Studies of Nanometer Polymersomes Across Tissue Engineered Human Oral Mucosa" *Pharmaceutical Research*, 26:1718-1728.

Hearnden, V. et al. (2009) "Penetration of Polymersome Drug and Gene Delivery Nanoparticles Into in Vitro Models of Head and Neck Cancer and Tissue Engineered Oral Mucosa" *Oral Abstracts/Oral Oncology*, Supplement 3; p. 66, Abstract O31.

Helcké, G.A. et al. (1968) "Electron Resonance Studies of Haemoglobin Derivatives. III. Line-Width and g-Value Measurements of Acid-Met Myoglobin and of Met Myoglobin Azide Derivatives" *Proceedings of the Royal Society of London Series B—Biological Sciences*, 169:275-288.

Helfand, C. (Jul. 23, 2013) "Top twenty orphan drugs by 2018" *Fierce Pharma.com. Business Insights: Global* [online]. Retrieved from: http://www.fiercepharma.com/special-reports/top-20-orphan-drugs-2018, 2 pages.

Helfrich, W. and Servuss, R.-M. (1984) "Undulations, Steric Interactions and Cohesion of Fluid Membranes" *Il Nuovo Cimento*, 3D(1):137-151.

Henke, M. et al. (1999) "Erythropoietin for Patients Undergoing Radiotherapy: a Pilot Study" *Radiotherapy and Oncology*, 50:185-190.

(56) References Cited

OTHER PUBLICATIONS

Henselwood, F. et al. (1998) "Water-Soluble Porous Nanospheres" *Macromolecules*, 31:4213-4217.

Hentze, H.-P. et al. (Jul. 30, 1999) "Lyotropic Mesophases of Poly(ethylene oxide)-b-poly(butadiene) Diblock Copolymers and Their Cross-Linking to Generate Ordered Gels" *Macromolecules*, 32(18):5803-5809.

Herold, S. et al. (2001) "Kinetic and Mechanistic Studies of the NO-Mediated Oxidation of Oxymyoglobin and Oxyhemoglobin" *Biochemistry*, 40:3385-3395.

Hillman, G.G. et al. (2007) "Progression of renal cell carcinoma is inhibited by genistein and radiation in an orthotopic model" *BMC Cancer*, 7:4; doi:10.1186/1471-2407-7-4, 12 pages.

Hillmyer, M.A. and Bates, F.S. (1996) "Synthesis and Characterization of Model Polyalkane-Poly (ethylene oxide) Block Copolymers" *Macromolecules*, 29:6994-7002.

Hillmyer, M.A. et al. (Feb. 16, 1999) "Complex Phase Behavior in Solvent-Free Nonionic Surfactants" *Science*, 271:976-978.

Hochachka, P.W. (Oct. 26, 1999) "The Metabolic Implications of Intracellular Circulation" *PNAS*, 96:12233-12239.

Höckel, M. et al. (1993) "Intratumoral pO2 Predicts Survival in Advanced Cancer of the Uterine Cervix" Radiotherapy and Oncology, 26:45-50.

Höckel, M. et al. (1993) "Tumor Oxygenation: A New Predictive Parameter in Locally Advanced Cancer of the Uterine Cervix" *Gynecologic Oncology*, 51:141-149.

Höckel, M. et al. (Oct. 1, 1996) "Association Between Tumor Hypoxia and Malignant Progression in Advanced Cancer of the Uterine Cervix" *Cancer Research* 56:4509-4515.

Hodi, F.S. et al. (2013) "MPDL3280A (anti-PDL1): Clinical activity, safety and biomarkers of an engineered PD-L1 antibody in patients with locally advanced or metastatic tumors" *European Journal of Cancer*, 49:S184, Abstract 879, 1 page.

Hoogsteen, I.J. et al. (2007) "The Hypoxic Tumour Microenvironment, Patient Selection and Hypoxia-modifying Treatments" *Clinical Oncology*, 19:385-396.

Hoskin, P.J. et al. (1999) "Hypoxic Radiosensitizers in Radical Radiotherapy for Patients with Bladder Carcinoma. Hyperbaric Oxygen, Misonidazole, and Accelerated Radiotherapy, Carbogen, and Nicotinamide" *Cancer*, 86:1322-1328.

Hudes, G. et al. (2007) "Temsirolimus, Interferon Alfa, or Both for Advanced Renal-Cell Carcinoma" *New England Journal of Medicine*, 356:2271-2281.

Hutson, T.E. (2013) "Axitinib versus sorafenib as first-line therapy in patients with metastatic renal cell carcinoma (mRCC)" *Journal of Clinical Oncology*, 31(suppl 6):Abstract LBA348, 1 page.

Hylander, B.L. et al. (2013) "Origin of the vasculature supporting growth of primary patient tumor xenografts" *Journal of Translational Medicine*, 11:110, 14 pages.

Janssen, H.L. et al. (Jul. 2005) "Hypoxia in Head and Neck Cancer: How Much, How Important?" *Head and Neck*, 27:622-638.

Kaelin, W.G. Jr. (2004) "The Von Hippel-Lindau Tumor Suppressor Gene and Kidney Cancer" *Clin Cancer Res*, 10(Suppl):6290s-6295s.

Kaelin, W.G. Jr. (Jun. 2005) "ROS: Really Involved in Oxygen Sensing" *Cell Metabolism*, 1:357-358.

Kaelin, W.G. Jr. (Jan. 15, 2007) "The von Hippel-Lindau tumor suppressor protein and clear cell renal carcinoma" *Clin Cancer Res*, 13(2 Suppl):680s-684s.

Kanner, J. et al. (1991) "Nitric-Oxide as an Antioxidant" *Archives of Biochemistry and Biophysics*, 289:130-136.

Karar, J. et al. (2009) "Modulating the Tumor Microenvironment to Increase Radiation Responsiveness" *Cancer Biology & Therapy*, 8:1994-2001.

Katz, D. et al. (2009) "On the Path to Seeking Novel Radiosensitizers" *International Journal of Radiation Oncology Biology Physics*, 73:988-996.

Katz, J.S. et al. (2009) "Membrane Stabilization of Biodegradable Polymersomes" *Langmuir*, 25:4429-4434.

Kersey, F.R. et al. (2010) "Stereocomplexed Poly(lactic acid)-Poly(ethylene glycol) Nanoparticles with Dual-Emissive Boron Dyes for Tumor Accumulation" *ACS Nano*, 4:4989-4996.

Keyes, S.R. et al. (Aug. 1985) "Porfiromycin as a Bioreductive Alkylating Agent with Selective Toxicity to Hypoxic EMT6 Tumor Cells in vivo and in vitro" *Cancer Research*, 45:3642-3645.

Keyes, S.R. et al. (Jan. 1985) "Enhancement of Mitomycin C Cytotoxicity to Hypoxic Tumor Cells by Dicoumarol in vivo and in vitro" *Cancer Research*, 45:213-216.

Kim, K.T. et al. (2009) "A Polymersome Nanoreactor with Controllable Permeability Induced by Stimuli-Responsive Block Copolymers" *Advanced Materials*, 21:2787-2791.

Kim, M.S. and Lee, D.S. (2010) "Biodegradable and pH-Sensitive Polymersome with Tuning Permeable Membrane for Drug Delivery Carrier" *Chemical Communications*, 46:4481-4483.

Kirpotin, D. et al. (1996) "Liposomes with detachable polymer coating: destabilization and fusion of dioleoyphosphatidylethanolamine vesicles triggered by cleavage of surface-grafted poly(ethylene glycol)" *FEBS Letters*, 388:115-118.

Knocke, T-H. et al. (1999) "Intratumoral $pO_2$-Measurements as Predictive Assay in the Treatment of Carcinoma of the Uterine Cervix" *Radiotherapy and Oncology*, 53:99-104.

Kobayashi, M. et al. (May 2010) "Establishment and Characterization of Transplantable, Luminescence Labeled Rat Renal Cell Carcinoma Cell Lines" *J Urol*, 183:2029-2035.

Kobayashi, M. et al. (2012) "Effect of host immunity on metastatic potential in renal cell carcinoma: the assessment of optimal in vivo models to study metastatic behavior of renal cancer cells" *Tumor Biology*, 33:551-559.

Koch, C.J. et al. (2001) "Pharmacokinetics of EF5 [2-(2-nitro-1-H-imidazol-1-yl)-N-(2,2,3,3,3-pentafluoropropyl) acetamide] in human patients: Implications for hypoxia measurements in vivo by 2-nitrolmidazoles" *Cancer Chemother Pharmacol*, 48:177-187.

Koltover, I. et al. (Jul. 3, 1998) "An Inverted Hexagonal Phase of Cationic Liposome-DNA Complexes Related to DNA Release and Delivery" *Science*, 281:78-81.

Komatsu, T. et al. (1997) "Solid Vesicle Membrane Made of meso-Tetrakis [(bixinylamino)-o-phenyl]porphyrins" *J Am Chem Soc*, 119:11660-11665.

Kondo, A. et al. (Oct. 2001) "Hypoxia-Induced Enrichment and Mutagenesis of Cells That Have Lost DNA Mismatch Repair" *Cancer Research*, 61:7603-7607.

Kondo, K. et al. (2002) "Comprehensive mutational analysis of the VHL gene in sporadic renal cell carcinoma: relationship to clinicopathological parameters" *Genes Chromosomes Cancer*, 34:58-68.

Kondo, K. et al. (2002) "Inhibition of HIF is necessary for tumor suppression by the von Hippel-Lindau protein" *Cancer Cell*, 1:237-246.

Kong, G. et al. (Aug. 15, 2000) "Hyperthermia Enables Tumor-Specific Nanoparticle Delivery: Effect of Particle Size" *Cancer Research*, 60:4440-4445.

Kong, G. et al. (Apr. 1, 2001) "Characterization of the effect of hyperthermia on nanoparticle extravasation from tumor vasculature" *Cancer Research*, 61:3027-3032.

Kooyman, G.L. (1998) "The Physiological Basis of Diving to Depth: Birds and Mammals" *Annual Review of Physiology*, 60:19-32.

Lam, J.S. et al. (2005) "Novel approaches in the therapy of metastatic renal cell carcinoma" *World Journal of Urology*, 23:202-212.

Larkin, J. et al. (2012) "Efficacy of Sequential Treatment with Sunitinib-Everolimus in an Orthotopic Mouse Model of Renal Cell Carcinoma" *Anticancer Research*, 32:2399-2406.

Lavey, R. S. and Dempsey, W.H. (1993) "Erythropoietin Increases Hemoglobin in Cancer-Patients During Radiation Therapy" *International Journal of Radiation Oncology Biology Physics*, 27:1147-1152.

Lee J. et al. (1996) "Direct relationship between radiobiological hypoxia in tumors and monoclonal antibody detection of EF5 cellular adducts" *International Journal of Cancer*, 67:372-378.

Lee, D-J. et al. (1989) "A Phase I/II Study of the Hypoxic Cell Sensitizer Misonidazole as an Adjunct to High Fractional Dose

(56) References Cited

OTHER PUBLICATIONS

Radiotherapy in Patients with Unresectable Squamous Cell Carcinoma of the Head and Neck: A RTOG Randomized Study (#79-04)" *International Journal of Radiation Oncology Biology Physics*, 16:465-470.
Lee, D-J. et al. (1995) "Results of an rtog phase-III trial (RTOG 85-27) comparing radiotherapy plus etanidazole with radiotherapy alone for locally advanced head and neck carcinomas" *International Journal of Radiation Oncology Biology Physics*, 32:567-576.
Lee, D-J. et al. (1998) "Concurrent Tirapazamine and Radiotherapy for Advanced Head and Neck Carcinomas: A Phase II Study" *International Journal of Radiation Oncology Biology Physics*, 42:811-815.
Lee, Y-S. et al. (Feb. 1, 2005) "Coexpression of erythropoietin and erythropoietin receptor in von Hippel-Lindau disease-associated renal cysts and renal cell carcinoma" *Clin Cancer Res*, 11:1059-1064.
Letchford, K. et al. (2007) "A review of the formation and classification of amphiphilic block copolymer nanoparticulate structures: micelles, nanospheres, nanocapsules and polymersomes", *Eur J Pharm Biopharm*, 65:259-269.
Lim, S.H. et al. (2009) "Effect of Combination of Anticancer Agents and Nitroimidazoles on the Survival of Human Hepatocellular Carcinoma Cells under Hypoxic Conditions" *Journal of the Korean Surgical Society*, 76:337-347. Korean with English Summary on p. 337.
Lin, J.J. et al. (2004) "The Effect of Polymer Chain Length and Surface Density on the Adhesiveness of Functionalized Polymersomes" *Langmuir*, 20:5493-5500.
Lin, J.J. et al. (2006) "Adhesion of Antibody-Functionalized Polymersomes" *Langmuir*, 22:3975-3979.
Lin, Z. et al. (1992) "Cryogenic Electron Microscopy of Rodlike or Wormlike Micelles in Aqueous Solutions of Nonionic Surfactant Hexaethylene Glycol Monohexadecyl Ether" *Langmuir*, 8:2200-2205.
Lipowsky and Sackmann (Eds.) (1995) *Handbook of Biological Physics. vol. 1: Structure and Dynamics of Membranes from Cells to Vesicles*. Amsterdam: Elsevier Science; Chapters 1-10, 513 pages.
Liu, G-Y. et al. (2012) "Biocompatible and biodegradable polymersomes as delivery vehicles in biomedical applications" *Soft Matter*, 8:8811-8821.
Liu, J. et al. (Nov. 2015) "Efficient delivery of nuclease proteins for genome editing in human stem cells and primary cells" *Nat Protocols*, 10(11):1842-1859.
Liu, S. and O'Brien, D.F. (Aug. 7, 1999) "Cross-Linking Polymerization in Two-Dimensional Assemblies: Effect of the Reactive Group Site" *Macromolecules*, 32:5519-5524.
Lomas, H. et al. (2011) "Polymersome-Loaded Capsules for Controlled Release of DNA" *Small*, 7(14):2109-2119.
Longo, M.L. et al. (Sep. 1997) "Interaction of the Influenza Hemagglutinin Fusion Peptide with Lipid Bilayers: Area Expansion and Permeation" *Biophys J*, 73:1430-1439.
Ma, W.W. and Adjei, A.A. (2009) "Novel agents on the horizon for cancer therapy" *CA Cancer J Clin*, 59:111-137.
Malik, A. et al. (Oct. 1, 2012) "Myoglobin Unfolding in Crowding and Confinement" *J Phys Chem*, 116:12895-12904.
Marzilli, L. et al. (2000) "Peptide sequence information derived by pronase digestion and ammonium sulfate in-source decay matrix-assisted laser desorption/ionization time-of-flight mass spectrometry" *J Am Soc Spectrom*, 11:1000-1008.
Massignani, M. et al. (2009) "Controlling Cellular Uptake by Surface Chemistry, Size, and Surface Topology at the Nanoscale" *Small*, 5:2424-2432.
McGee, M.C. et al. (2010) "Improved Intratumoral Oxygenation Through Vascular Normalization Increases Glioma Sensitivity to Ionizing Radiation" *International Journal of Radiation Oncology Biology Physics*, 76:1537-1545.

Melichar, B. et al. (2008) "First-line bevacizumab combined with reduced dose interferon-alpha2a is active in patients with metastatic renal cell carcinoma" *Ann Oncol*, 19:1470-1476.
Meng, F.H. et al. (2005) "Biodegradable polymersomes as a basis for artificial cells: encapsulation, release and targeting" *J Control Release*, 101:187-198.
Meric-Bernstam, F. et al. (May 1, 2009) "Targeting the mTOR signaling network for cancer therapy" *J Clin Oncol*, 27:2278-2287.
Merriam-Webster, Inc. "Electrolyte" in *Merriam-Webster Collegiate® Dictionary*. Tenth Edition. Springfield, Massachusetts, USA: 2002, p. 371.
Miralbell, R. et al. (1999) "Accelerated Radiotherapy, Carbogen, and Nicotinamide in Glioblastoma Multiforme: Report of European Organization for Research and Treatment of Cancer Trial 22933" *J Clin Oncol*, 17:3143-3149.
Moeller, B.J. and Dewhirst, M.W. (Sep. 2004) "Raising the Bar. How HIF-1 Helps Determine Tumor Radiosensitivity" *Cell Cycle*, 3:1107-1110.
Moeller, B.J. et al. (Aug. 2005) "Pleiotropic Effects of HIF-1 Blockade on Tumor Radiosensitivity" *Cancer Cell*, 8:99-110.
Moeller, B.J. et al. (2006) "HIF-1 and tumour radiosensitivity" *British Journal of Cancer*, 95:1-5.
Moeller, B.J. et al. (2007) "Hypoxia and Radiotherapy: Opportunities for Improved Outcomes in Cancer Treatment" *Cancer and Metastasis Reviews*, 26:241-248.
Molina, A.M. et al. (2012) "Phase 1 trial of everolimus plus sunitinib in patients with metastatic renal cell carcinoma" *Cancer*, 118:1868-1876.
Molino, D. et al. (2006) "The history of von Hippel-Lindau disease" *J Nephrol*, 19(Supp):S119-S123.
Moore, E.E. et al. (2009) "Human Polymerized Hemoglobin for the Treatment of Hemorrhagic Shock when Blood Is Unavailable: The USA Multicenter Trial" *Journal of the American College of Surgeons*, 208:1-13.
Motzer, R.J. et al. (2008) "Efficacy of everolimus in advanced renal cell carcinoma: a double-blind, randomised, placebo-controlled phase III trial" *Lancet*, 372:449-456.
Motzer, R.J. et al. (2009) "Overall survival and updated results for sunitinib compared with interferon alfa in patients with metastatic renal cell carcinoma" *J Clin Oncol*, 27:3584-3590.
Motzer, R.J. et al. (2009) "Phase I Trial of Sunitinib Malate plus Interferon-alpha for Patients with Metastatic Renal Cell Carcinoma" *Clinical Genitourinary Cancer*, 7:28-33.
Motzer, R.J. et al. (2012) "Tivozanib versus sorafenib as initial targeted therapy for patients with advanced renal cell carcinoma: Results from a phase III randomized, open-label, multicenter trial" *J Clin Oncol*, 30(Suppl 15):277s, Abstract 4501, 1 page.
Motzer, R.J. et al. (2013) "A phase 3 comparative study of nivolumab (anti-PD-1; BMS-936558; ONO-4538) versus everolimus in patients with advanced or metastatic renal cell carcinoma (mRCC) previously treated with anti-angiogenic therapy" *BJU International*, 112 Suppl 3:10, Abstract 15.
Motzer, R.J. et al. (2014) "Dovitinib versus sorafenib for third-line targeted treatment of patients with metastatic renal cell carcinoma: an open-label, randomised phase 3 trial" *Lancet Oncology*, 15:286-296.
Mourant, J.R. et al. (Oct. 1993) "Ligand Binding to Heme Proteins: II. Transitions in the Heme Pocket of Myoglobin" *Biophysical Journal*, 65:1496-1507.
Mozzarelli, A. et al. (2010) "Haemoglobin-based oxygen carriers: research and reality towards an alternative to blood transfusions", *Blood Transfus*, 8(Suppl 3):s59-s68.
Mueller, A. et al. (Aug. 22, 1999) "Light-Stimulated Destabilization of PEG-Liposomes" *Polymer Preprints (ACS)*, 40(2):205-206.
Mundt, A.J. et al. (1998) "Race and Clinical Outcome in Patients with Carcinoma of the Uterine Cervix Treated with Radiation Therapy" *Gynecologic Oncology*, 71:151-158.
Musumeci, F. et al. (2012) "Vascular Endothelial Growth Factor (VEGF) Receptors: Drugs and New Inhibitors" *J Med Chem*, 55:10797-10822.
Nagasawa, H. et al. (2006) "Design of Hypoxia-Targeting Drugs as New Cancer Chemotherapeutics" *Biological & Pharmaceutical Bulletin*, 29:2335-2342.

(56) References Cited

OTHER PUBLICATIONS

Najafi, F. and Sarbolouki, M.N. (2003) "Biodegradable Micelles/Polymersomes From Fumaric/Sebacic Acids and Poly(Ethylene Glycol)" *Biomaterials*, 24:1175-1182.

Natanson, C. et al. (2008) "Cell-free hemoglobin-based blood substitutes and risk of myocardial infarction and death. A meta-analysis" *JAMA*, 299(19):2304-2312.

Needham, D. and Zhelev, D.V. (1996) "The Mechanochemistry of Lipid Vesicles Examined by Micropipet Manipulation Techniques" in *Vesicles*. M. Rosoff (Ed.), New York: Dekker; Chapter 9, pp. 373-444.

Needham, D. and R.S. Nunn (Oct. 1990) "Elastic deformation and failure of lipid bilayer membranes containing cholesterol" *Biophys J*, 58:997-1009.

Netz, R.R. and M. Schick (Apr. 1996) "Pore formation and rupture in fluid bilayers" *Phys Rev E*, 53(4): 3875-3885.

Nienhaus, G.U. et al. (1994) "Ligand Binding to Heme Proteins: The Effect of Light on Ligand-Binding in Myoglobin" *Biochemistry*, 33:13413-13430.

Ordway, G.A. and Garry, D.J. (2004) "Myoglobin: An Essential Hemoprotein in Striated Muscle" *Journal of Experimental Biology*, 207:3441-3446.

Overgaard, J. (1989) "Sensitization of Hypoxic Tumor-Cells—Clinical Experience" *International Journal of Radiation Biology*, 56:801-811.

Overgaard, J. and Horsman, M.R. (1996) "Modification of Hypoxia-Induced Radioresistance in Tumors by the Use of Oxygen and Sensitizers" *Seminars in Radiation Oncology*, 6:10-21.

Overgaard, J. et al. (1989) "Misonidazole Combined with Radiotherapy in the Treatment of Carcinoma of the Uterine Cervix" *Int J Radiation Oncology Biol Phys*, 16:1069-1072.

Overgaard, J. et al. (1989) "Misonidazole Combined with Split-Course Radiotherapy in the Treatment of Invasive Carcinoma of Larynx and Pharynx: Report From the Dahanca 2 Study" *Int J Radiation Oncology Biol Phys*, 16:1065-1068.

Overgaard, J. et al. (1998) "A Randomized Double-Blind Phase III Study of Nimorazole as a Hypoxic Radiosensitizer of Primary Radiotherapy in Supraglottic Larynx and Pharynx Carcinoma. Results of the Danish Head and Neck Cancer Study (DAHANCA) Protocol 5-85" *Radiotherapy and Oncology*, 46:135-146.

Palaparthy, R. et al. (2000) "Current Aspects in Pharmacology of Modified Hemoglobins" *Adv Drug Deliv Rev*, 40:185-198.

Palmer, A.F. et al. (2009) "Tangential flow filtration of hemoglobin" *Biotechnology Progress*, 25:189-199.

Palmer, G.M. et al. (2009) "Quantitative Diffuse Reflectance and Fluorescence Spectroscopy: Tool to Monitor Tumor Physiology in Vivo" *Journal of Biomedical Optics*, 14(2):024010, 8 pages.

Palmer, G.M. et al. (2010) "Non-Invasive Monitoring of Intra-Tumor Drug Concentration and Therapeutic Response Using Optical Spectroscopy" *J Control Release*, 142:457-464.

Palmer, G.M. et al. (2010) "Optical imaging of tumor hypoxia dynamics" *J Biomed Opt*, 15(6):066021, 7 pages.

Palmer, G.M. et al. (2011) "In vivo optical molecular imaging and analysis in mice using dorsal window chamber models applied to hypoxia, vasculature and fluorescent reporters" *Nat Protoc*, 6:1355-1366.

Papadopoulou, M.V. et al. (2000) "4-[3-(2-Nitro-1-imidazolyl)propylamino]-7-chloroquinoline Hydrochloride (NLCQ-1), a Novel Bioreductive Agent as Radiosensitizer in Vitro nd in Vivo: Comparison with Tirapazamine" *Oncology Research*, 12:325-333.

Papadopoulou, M.V. et al. (2000) "4-[3-(2-Nitro-1-imidazolyl)propylamino]-7-chloroquinoline Hydrochloride (NLCQ-1), a Novel Bioreductive Compound as a Hypoxia-Selective Cytotoxin" *Oncology Research*, 12:185-192.

Patel, P.H. et al. (2009) "Phase I Study Combining Treatment with Temsirolimus and Sunitinib Malate in Patients with Advanced Renal Cell Carcinoma" *Clinical Genitourinary Cancer*, 7:24-27.

Patil, S. et al. (Dec. 2012) "Improvement in Overall Survival of Patients with Advanced Renal Cell Carcinoma: Prognostic Factor Trend Analysis from an International Data Set of Clinical Trials" *J Urol*, 188:2095-2100.

Patton, J.N. and Palmer, A.F. (2006) "Physical Properties of Hemoglobin—Poly(acrylamide) Hydrogel-Based Oxygen Carriers: Effect of Reaction pH" *Langmuir*, 22:2212-2221.

Petrov, A.G. and Bivas, I. (1984) "Elastic and Flexoelectric Aspects of Out-of-Plane Fluctuations in biological and Model Membranes" *Prog Surf Sci*, 16:389-511.

Privalov, P.L. et al. (1986) "Cold Denaturation of Myoglobin" *J Mol Biol*, 190:487-498.

Rabotyagova, O.S. et al. (2009) "Self-Assembly of Genetically Engineered Spider Silk Block Copolymers" *Biomacromolecules*, 10:229-236.

Rameez, S. et al. (2012) "Reactivity of Polymersome Encapsulated Hemoglobin with Physiologically Important Gaseous Ligands: Oxygen, Carbon Monoxide, and Nitric Oxide" *Macromolecules*, 45:2385-2389.

Raval, R.R. et al. (Jul. 2005) "Contrasting properties of hypoxia-inducible factor 1 (H1F-1) and HIF-2 in von Hippel-Lindau-associated renal cell carcinoma" *Mol Cell Biol*, 25:5675-5686.

Rini, B. et al. (Nov. 20, 2008) "Bevacizumab plus interferon alfa compared with interferon alfa monotherapy in patients with metastatic renal cell carcinoma: CALGB 90206" *J Clin Oncol*, 26:5422-5428.

Rini, B. et al. (Dec. 15, 2012) "AMG 386 in combination with sorafenib in patients with metastatic clear cell carcinoma of the kidney" *Cancer*, 118:6152-6161.

Rischin, D. et al. (Jun. 20, 2010) "Tirapazamine, Cisplatin, and Radiation Versus Cisplatin and Radiation for Advanced Squamous Cell Carcinoma of the Head and Neck (TROG 02.02, HeadSTART): A Phase III Trial of the Trans-Tasman Radiation Oncology Group" *J Clin Oncol*, 28:2989-2995.

Robbins, G.P. et al. (2009) "Photoinitiated Destruction of Composite Porphyrin-Protein Polymersomes", *J Am Chem Soc*, 131:3872-3874.

Robert, C. et al. (2013) "Drug of the year: Programmed Death-1 receptor/Programmed Death-1 Ligand-1 receptor monoclonal antibodies" *European Journal of Cancer*, 49:2968-2971.

Roberts, K.B. et al. (2000) "Interim Results of a Randomized Trial of Mitomycin C as an Adjunct to Radical Radiotherapy in the Treatment of Locally Advanced Squamous-Cell Carcinoma of the Cervix" *Int J Cancer*, 90:206-223.

Robinson, M.F. et al. (1995) "Increased Tumor Oxygenation and Radiation Sensitivity in Two Rat Tumors by a Hemoglobin-Based, Oxygen-Carrying Preparation" *Artif Cells Blood Substit Immobil Biotechnol*, 23:431-438.

Rockwell, S. (1997) "Oxygen Delivery: Implications for the Biology and Therapy of Solid Tumors" *Oncology Research*, 9:383-390.

Rockwell, S. et al. (2009) "Hypoxia and Radiation Therapy: Past History, Ongoing Research, and Future Promise" *Current Molecular Medicine*, 9:442-458.

Rofstad, E.K. et al. (2000) "Hypoxia-Induced Treatment Failure in Advanced Squamous Cell Carcinoma of the Uterine Cervix Is Primarily Due to Hypoxia Induced Radiation Resistance Rather than Hypoxia-Induced Metastasis" British Journal of Cancer, 83:354-359.

Rosenthal, D.I. et al. (1999) "A Phase I Single-Dose Trial of Gadolinium Texaphyrin (Gd-Tex), a Tumor Selective Radiation Sensitizer Detectable by Magnetic Resonance Imaging" *Clinical Cancer Research*, 5:739-745.

Rowinsky, E.K. (Oct. 1999) "Novel Radiation Sensitizers Targeting Tissue Hypoxia" *Oncology*, 13:61-70.

Rudat, V. et al. (2000) "Repeatability and Prognostic Impact of the Pretreatment PO2 Histography in Patients with Advanced Head and Neck Cancer" Radiotherapy and Oncology, 57:31-37.

Sabatini, D.M. (Sep. 2006) "mTOR and cancer: insights into a complex relationship" *Nat Rev Cancer*, 6:729-734.

Sakai, H. et al. (1996) "Functional Evaluation of Hemoglobin- and Lipidheme-vesicles as Red Cell Substitutes" *Polymers for Advanced Technologies*, 7:639-644.

(56) References Cited

OTHER PUBLICATIONS

Sakai, H. et al. (2008) "NO and CO Binding Profiles of Hemoglobin Vesicles as Artificial Oxygen Carriers" *Biochimica et Biophysica Acta*, 1784:1441-1447.

Salumbides, B.C. et al. (Dec. 2009) "Pre-clinical models of renal carcinoma and their utility in drug development" *Curr Protoc Pharmacol*, 47:14.13.1-14.13.19.

Sartorelli, A.C. et al. (1994) "Mitomycin C: A Prototype Bioreductive Agent" *Oncology Research*, 6:501-508.

Saunders, M. and S. Dische (1996) "Clinical Results of Hypoxic Cell Radiosensitisation from Hyperbaric Oxygen to Accelerated Radiotherapy, Carbogen and Nicotinamide" *British Journal of Cancer*, 74(Suppl. 27):S271-S278.

Schatz, C. et al. (2009) "Polysaccharide-Block-Polypeptide Copolymer Vesicles: Towards Synthetic Viral Capsids" *Angew Chem Int Ed*, 48:2572-2575.

Schmid-Schönbein, H. et al. (1986) "Spectrin, Red Cell Shape and Deformability. I. Membrane Curvature in Genetic Spectrin Deficiency" *Blut*, 52(3):131-147.

Schraml, P. et al. (2002) "*VHL* mutations and their correlation with tumour cell proliferation, microvessel density, and patient prognosis in clear cell renal cell carcinoma" *J Pathol*, 196:186-193.

Seifert, U. et al. (Jul. 15, 1999) "Shape transformations of vesicles: Phase diagram for spontaneous-curvature and bilayer-coupling models" *Phys Rev A*, 44(2):1182-1202.

Seow, W.Y. and Y-Y. Yang (2009) "A Class of Cationic Triblock Amphiphilic Oligopeptides as Efficient Gene-Delivery Vectors" *Adv Mater*, 21:86-90.

Shasha, D. (Jul. 2001) "The Negative Impact of Anemia on Radiotherapy and Chemoradiation Outcomes" *Seminars in Hematology*, 38:8-15.

Shasha, D. et al. (2003) "Once-Weekly Dosing of Epoetin-Alfa Increases Hemoglobin and Improves Quality of Life in Anemic Cancer Patients Receiving Radiation Therapy Either Concomitantly or Sequentially with Chemotherapy" *Cancer*, 98:1072-1079.

Shibamoto, Y. et al. (2001) "In Vivo Evaluation of a Novel Antitumor Prodrug, 1-(2'-Oxopropyl)-5-Fluorouracil (OFU001), Which Releases 5-Fluorouracil Upon Hypoxic Irradiation" *International Journal of Radiation Oncology Biology Physics*, 49:407-413.

Shibayu, M. (2008) "Vascular endothelial growth factor-dependent and -independent regulation of angiogenesis" *BMB Reports*, 41:278-286.

Shih, Y.C. et al. (2011) "Economic burden of renal cell carcinoma in the US. Part II—An updated analysis" *Pharmacoeconomics*, 29:331-341.

Shum, H.C. et al. (2008) "Microfluidic Fabrication of Monodisperse Biocompatible and Biodegradable Polymersomes with Controlled Permeability" *J Am Chem Soc*, 130:9543-9549.

Siemann, D.W. et al. (1998) "Potentiation of Cisplatin Activity by the Bioreductive Agent Tirapazamine" *Radiotherapy and Oncology*, 47:215-220.

Sisson, T.M. et al. (1996) "Cross-Linking Polymerizations in Two-Dimensional Assemblies" *Macromolecules*, 29:8321-8329.

Sivanand, S. et al. (Jun. 6, 2012) "A Validated Tumorgraft Model Reveals Activity of Dovitinib Against Renal Cell Carcinoma" *Science Translational Medicine*, 4:137ra75, including Editor's Summary, 18 pages.

Sivanesaratnam, V. et al. (1989) "Mitomycin C Adjuvant Chemotherapy After Wertheim's Hysterectomy for Stage-IB Cervical Cancer" *Cancer*, 64:798-800.

Smaldone, M.C. et al. (2011) "Adjuvant and Neoadjuvant Therapies in High-Risk Renal Cell Carcinoma" *Hematology/Oncology Clinics of North America*, 25:765-791.

Sonpavde, G. and T.K. Choueiri (2014) "Precision medicine for metastatic renal cell carcinoma" *Urologic Oncology*, 32:5-15.

Sonpavde, G. et al. (2014) "Fibroblast growth factor receptors as therapeutic targets in clear-cell renal cell carcinoma" *Expert Opinion on Investigational Drugs*, 23:305-315.

Sonveaux, P. et al. (2005) "Oxygen Regulation of Tumor Perfusion by S-Nitrosohemoglobin Reveals a Pressor Activity of Nitric Oxide" *Circulation Research*, 96:1119-1126.

Sorg, B.S. et al.(2005) "Hyperspectral Imaging of Hemoglobin Saturation in Tumor Microvasculature and Tumor Hypoxia Development" *Journal of Biomedical Optics*, 10(4):044004, 11 pages.

Sorg, B.S. et al. (Jan./Feb. 2008) "Spectral Imaging Facilitates Visualization and Measurements of Unstable and Abnormal Microvascular Oxygen Transport in Tumors" *Journal of Biomedical Optics*, 13(1):014026, 11 pages.

Stadler, P. et al. (1998) "Changes in Tumor Oxygenation During Combined Treatment with Split-Course Radiotherapy and Chemotherapy in Patients with Head and Neck Cancer" *Radiotherapy and Oncology*, 48:157-164.

Stadler, P. et al. (1999) "Influence of the Hypoxic Subvolume on the Survival of Patients with Head and Neck Cancer" *International Journal of Radiation Oncology Biology Physics*, 44(4):749-754.

Stefely, J. et al. (1988) "Permeability Characteristics of Lipid Bilayers from Lipoic Acid Derived Phosphatidylcholines: Comparison of Monomeric, Cross-Linked and Non-Cross-Linked Polymerized Membranes" *J Am Chem Soc*, 110:7463-7469.

Sternberg, C.N. et al. (2013) "A randomised, double-blind phase III study of pazopanib in patients with advanced and/or metastatic renal cell carcinoma: Final overall survival results and safety update" *European Journal of Cancer*, 49:1287-1296.

Strube, A. et al. (2010) "Characterization of a new renal cell carcinoma bone metastasis mouse model" *Clin Exp Metastasis*, 27:319-330.

Stüben, G. et al. (1998) "The Effect of Combined Nicotinamide and Carbogen Treatments in Human Tumour Xenografts: Oxygenation and Tumour Control Studies" *Radiotherapy and Oncology*, 48:143-148.

Svetina, S. et al. (1989) "Membrane bending energy and shape determination of phospholipid vesicles and red blood cells" *Eur Biophys J*, 17:101-111.

Szleifer, I. et al. (May 9, 1988) "Curvature Elasticity of Pure and Mixed Surfactant Films" *Phys Rev Lett*, 60(19):1966-1969.

Takeshi, K. et al. (1998) "Definitive radiotherapy combined with high-dose-rate brachytherapy for stage iii carcinoma of the uterine cervix: retrospective analysis of prognostic factors concerning patient characteristics and treatment parameters" *International Journal of Radiation Oncology Biology Physics*, 41:319-327.

Tang, P.A. and Heng, D.Y.C. (2013) "Programmed death 1 pathway inhibition in metastatic renal cell cancer and prostate cancer" *Current Oncology Reports*, 15:98-104.

Tao, Z. et al. (Sep. 2014) "Microparticle, nanoparticle, and stem cell-based oxygen carriers as advanced blood substitutes" *Trends Biotechnol*, 32(9):466-473.

Teicher, B.A. (Apr. 1995) "Physiological Mechanisms of Therapeutic Resistance. Blood Flow and Hypoxia" *Hematology/Oncology Clinics of North America*, 9:475-506.

Teicher, B.A. et al. (1992) "Effect of a Bovine Hemoglobin Preparation on the Response of the FSaIIC Fibrosarcoma to Chemotherapeutic Alkylating Agents" *J Cancer Res Clin Oncol*, 118:123-128.

Teicher, B.A. et al. (1993) "Effect of Hemoglobin Solution on the Response of Intracranial and Subcutaneous Tumors to Antitumor Alkylating-Agents" *Cancer Chemother Pharmacol*, 33:57-62.

Teicher, B.A. et al. (1993) "Oxygenation of Tumors by a Hemoglobin Solution" *J Cancer Res Clin Oncol*, 120:85-90.

Teicher, B.A. et al. (1994) "Oxygenation of the Rat-9L Gliosarcoma and the Rat 13672 Mammary Carcinoma with Various Doses of a Hemoglobin Solution" *Artif Cells Blood Substit Immob Biotechnol*, 22:827-833.

Terman, D.S. et al. (Jan. 2013) "Sickle Erythrocytes Target Cytotoxics to Hypoxic Tumor Microvessels and Potentiate a Tumoricidal Response" *PLoS ONE*, 8:e52543, 11 pages.

Treat, J. et al. (1998) "Tirapazamine with Cisplatin in Patients with Advanced Non-Small-Cell Lung Cancer: A Phase II Study" *Journal of Clinical Oncology*, 16:3524-3527.

Uchegbu, I.F. et al. (1998) "Polymeric Chitosan-based Vesicles for Drug Delivery" *J Pharm Pharmacol*, 50:453-458.

(56) References Cited

OTHER PUBLICATIONS

Van Dongen, S.F.M. et al. (2008) "A Block Copolymer for Functionalisation of Polymersome Surfaces", *Macromolecular Rapid Communications*, 29:321-325.

Víteček, J. et al. (2012) "Arginine-Based Inhibitors of Nitric Oxide Synthase: Therapeutic Potential and Challenges" *Mediators of Inflammation*, 2012:Article ID 318087, 22 pages.

Von Pawel, J. et al. (2000) "Tirapazamine Plus Cisplatin Versus Cisplatin in Advanced Non-Small-Cell Lung Cancer: A Report of the International CATAPULT I Study Group" *J Clin Oncol*, 18:1351-1359.

Walsh, L. et al. (2006) "Efficacy of ablative high-dose-per-fraction radiation for implanted human renal cell cancer in a nude mouse model" *European Urology*, 50:795-800.

Walter, S. et al. (2012) "Multipeptide immune response to cancer vaccine IMA901 after single-dose cyclophosphamide associates with longer patient survival" *Nature Medicine*, 18:1254-1261.

Wang, et al. (2012) "A novel murine model of human renal cell carcinoma spinal metastasis" *Journal of Clinical Neuroscience*, 19:881-883.

Wang, F. et al. (2009) "Biodegradable Vesicular Nanocarriers Based on Poly(Epsilon-Caprolactone)-Block-Poly(Ethyl Ethylene Phosphate) for Drug Delivery" *Polymer*, 50:5048-5054.

Wang, L. et al. (2012) "Encapsulation of Biomacromolecules within Polymersomes by Electroporation" *Angew Chem Int Ed Engl*, 51:11122-11125.

Warriner, H.E. et al. (Feb. 16, 1996) "Lamellar Biogels: Fluid-Membrane-Based Hydrogels Containing Polymer Lipids" *Science*, 271:969-973.

Wasserman, T.H. et al. (1991) "Clinical-Trials with Etanidazole (SR-2508) by the Radiation Therapy Oncology Group (RTOG)" *Radiotherapy and Oncology*, 20:129-135.

Weitman, S. et al. (1999) "Evidence of Enhanced in Vivo Activity Using Tirapazamine with Paclitaxel and Paraplatin Regimens against the MV-522 Human Lung Cancer Xenograft" *Cancer Chemother Pharmacol*, 43:402-408.

Williams, K.J. et al. (2009) "In Vivo Activation of the Hypoxia-Targeted Cytotoxin AQ4N in Human Tumor Xenografts" *Molecular Cancer Therapeutics*, 8:3266-3275.

Wilson, D. et al. (1998) "Oxygen Distributions within R3230AC Tumors Growing in Dorsal Flap Window Chambers in Rats" *Adv Exp Med Biol*, 454:603-609.

Wiradharma, N. et al. (Mar. 2008) "Self-assembled Cationic Peptide Nanoparticles Capable of Inducing Efficient Gene Expression in Vitro" *Adv Funct Mater*, 18(6):943-951.

Wittenberg, J.B. and Wittenberg, B.A. (2003) "Myoglobin Function Reassessed" *Journal of Experimental Biology*, 206:2011-2020.

Won, Y-Y. et al. (Feb. 12, 1999) "Giant Wormlike Rubber Micelles" *Science*, 283:960-963.

Wood, C.G. and Filgin, R.A. (2013) "ADAPT: An Ongoing international phase 3 randomized trial of autologous dendritic cell Immunotherapy (AGS 003) plus standard treatment in advanced renal cell carcinoma (RCC)" *BJU International*, 112:11-12, Abstract 18.

Wouters, B.G. et al. (2002) "Hypoxia as a target for combined modality treatments" *European Journal of Cancer*, 38:240-257.

Yildiz, M.E. et al. (2007) "Formation and characterization of polymersomes made by a solvent injection method" *Polymers for Advanced Technologies*, 18:427-432.

Yu, M.H. et al. (2007) "Oxygen carriers and cancer chemo- and radiotherapy sensitization: bench to bedside and back" *Cancer Treatment Reviews*, 33:757-761.

Yu, Y. et al. (1998) "Morphogenic Effect of Solvent on Crew-Cut Aggregates of Amphiphilic Diblock Copolymers" *Macromolecules*, 31:1144-1154.

Yuen, J.S.P. et al. (2011) "Inhibition of angiogenic and non-angiogenic targets by sorafenib in renal cell carcinoma (RCC) in a RCC xenograft model" *British Journal of Cancer*, 104:941-947.

Zhan, H.W. et al., "Effect of carbogen on tumour oxygenation and 32P-colloid interstitial irradiation response" *Medical Science Monitor*, 16(1):BR11-BR16.

Zhang, G.Q. et al. (Sep. 2009) "A Dual-Emissive-Materials Design Concept Enables Tumour Hypoxia Imaging" *Nature Materials*, 8:747-751.

Zhang, X.L. et al. (2008) "Key parameters affecting the initial leaky effect of hemoglobin-loaded nanoparticles as blood substitutes", *Journal of Materials Science: Materials in Medicine*, 19:2463-2470.

Zhao, J. et al. (2007) "Preparation of hemoglobin-loaded nano-sized particles with porous structure as oxygen carriers" *Biomaterials*, 28:1414-1422.

\* cited by examiner

| Block copolymer | Protein | PSM size D [nm] | PSM size after loading D [nm] | Protein Encapsulation [mg/mL] | Protein loading, w/w% protein/polymer | Efficiency % |
|---|---|---|---|---|---|---|
| PEG-SS-b-PDEAEMA | CC | 55 | 59 | 0.010 | 5.0 | 100 |
| | BSA | 55 | 49 | 0.008 | 4.0 | 80.6 |
| PEG-B-PAAc-b-PNIPAM | BSA | 162 | 150 | 2.025 | 40.5 | 81 |
| | CC | 162 | 155 | 2.000 | 40.0 | 80 |
| | Lys | 162 | 149 | 1.615 | 32.3 | 64.6 |
| | Ova | 162 | 147 | 2.210 | 44.2 | 88.3 |
| PEG-b-PCL-PDEAEMA | BSA | 154 | 146 | 0.098 | 19.6 | 78.5 |
| | CC | 154 | 164 | 0.112 | 22.3 | 89.1 |
| | Lys | 154 | 150 | 0.105 | 21.0 | 84.3 |
| | Ova | 154 | 113 | 0.106 | 21.2 | 84.7 |
| | IgG | 154 | 158 | 0.112 | 22.4 | 89.6 |
| PEO-b-PCL | Hb (Human) | 100 | 110-140 | 0.000 | | 2.0-12.0 |
| PEO-b-PLA | Hb (Bovine) | 100 | 110-140 | 0.000 | | 4.0-20.0 |
| PEO-b-PBD | Hb | 100 | 100 | 0.081 | 8.1 | 2.7 |
| | | 100 | 100 | 0.365 | 36.5 | 12 |
| PEO-b-PPS | Ova | 200 | | 0.006 | 0.06 | 9±8 |
| | Ova | 200 | | 0.024 | 0.24 | 37±10 |
| | BSA | 200 | | 0.128 | 1.28 | 19±5 |
| | γ-Globulin | 200 | | 0.050 | 0.50 | 15±5 |
| PMPC-b-PDPA | BSA | 110 | 110-120 | 0.309 | 3.09 | 12.37 |
| | IgG | 110 | 110-120 | 0.000 | 0.00 | 9.00 |
| | Mb | 110 | 110-120 | 0.199 | 1.99 | 7.97 |
| | Lz | 110 | 110-120 | 0.159 | 1.59 | 6.36 |
| PS-PIAT | GOX | | | 0.625 | 125.0 | 25.00 |
| | CalB | | | 0.340 | 68.0 | 17.00 |
| | HRP | | | 0.625 | 125.0 | 25.00 |
| PS-b-PAA | CC | | | | | 66.00 |
| | Poly-L-Lysine | | | | | |
| | GFP | | | | | 35.00 |

FIG. 1

| Copolymer Name | Mn × 10³ PEO-b-PBD | Mw (kg/mol) | PDI* | Membrane Thickness (nm) | Vesicle Diameter (nm) |
|---|---|---|---|---|---|
| OB18 | 3.9-b-6.5 | 10400 | 1.10 | 14.8 | 205 |
| OB29 | 1.3-b-2.5 | 3800 | 1.04 | 9.6 | 132 |

FIG. 2

| Protein | Molecular Weight (kDa) | Before/After | Protein Content (mg/mL) | MPS (nm) | Efficiency (MW %) | Recovery Protein (mg/mL) | Recovery Protein (MW %) | Recovery Protein (MW %) |
|---|---|---|---|---|---|---|---|---|
| Myoglobin | 17 | Before | 2.68±0.75 | 13.39±3.75 | 4.70 | 2.21±1.19 | 11.07±5.97 | 3.82±1.07 | 19.10±5.36 |
|  |  | After | 1.98±0.43 | 9.19±2.15 | 3.48 | 1.13±0.44 | 5.64±2.21 | 2.05±0.80 | 10.31±3.98 |
| Hemoglobin | 64 | Before | 5.26±1.00 | 20.79±6.87 | 7.30 | 3.14±1.02 | 11.95±2.21 | 8.00±2.35 | 31.77±12.50 |
|  |  | After | 3.38±0.46 | 13.30±3.70 | 4.67 | 2.16±0.02 | 8.40±1.13 | 4.93±1.20 | 19.37±6.59 |
| Bovine Serum Albumin | 66 | Before | 3.53±2.38 | 15.60±11.02 | 13.69 |  |  |  |  |
|  |  | After | 3.49±1.13 | 15.42±5.15 | 13.53 |  |  |  |  |
| IgG | 150 | Before | 5.54±2.03 | 35.99±13.21 | 94.72 |  |  |  |  |
|  |  | After | 3.20±1.51 | 21.23±9.39 | 55.88 |  |  |  |  |
| Catalase | 250 | Before | 5.42±3.10 | 30.79±16.09 | 32.41 |  |  |  |  |
|  |  | After | 2.28±0.70 | 13.09±3.27 | 13.77 |  |  |  |  |
| Fibrinogen | 340 | Before | 5.37±0.76 | 26.10±3.49 | 27.48 |  |  |  |  |
|  |  | After | 3.05±0.39 | 14.82±1.72 | 15.60 |  |  |  |  |
| Apoferritin | 450 | Before | 1.99±1.02 | 8.51±4.28 | 17.92 |  |  |  |  |
|  |  | After | 1.73±1.23 | 7.57±5.73 | 15.94 |  |  |  |  |

FIG. 4

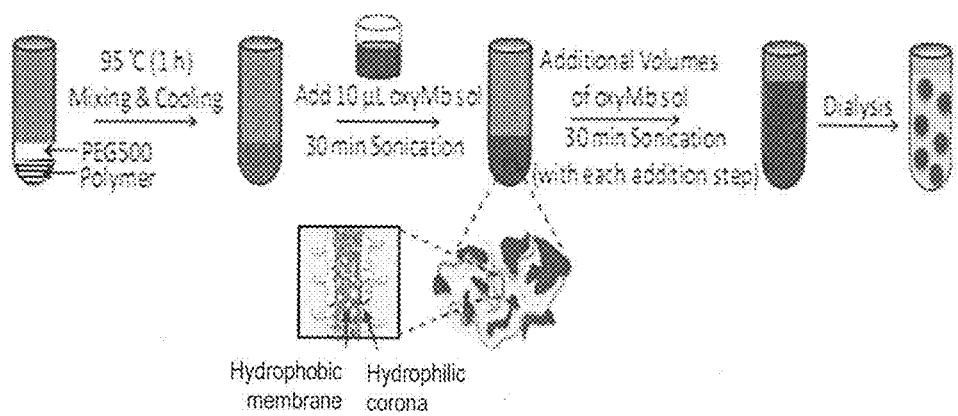
FIG. 7A
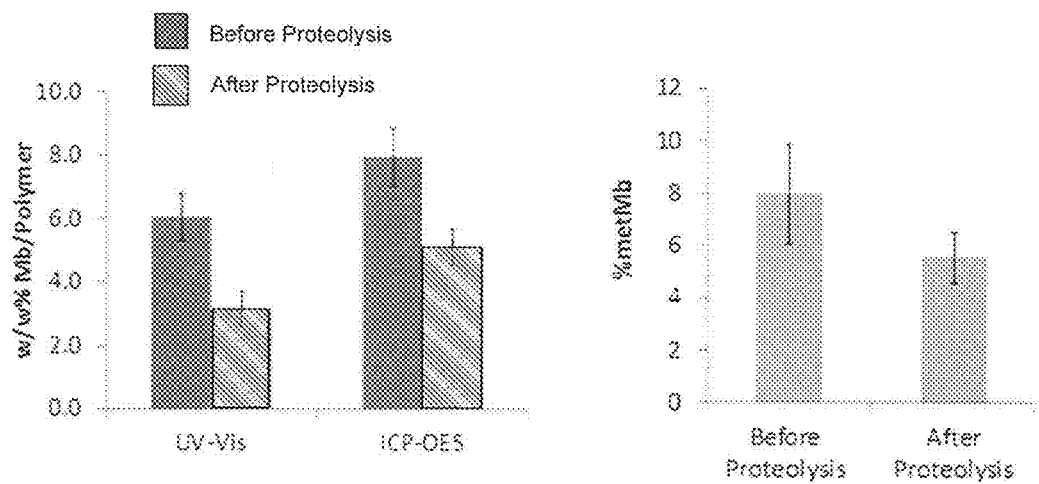
FIG. 7B
FIG. 7C

|  | Before Proteolysis | After Proteolysis |
|---|---|---|
| Final w/w% Mb/Polymer (by UV-vis) | 6.08 ± 0.75 | 3.17 ± 0.54 |
| Final w/w% Mb/Polymer (by ICP-OES) | 7.96 ± 0.91 | 5.10 ± 0.62 |
| % metMb | 7.98 ± 1.90 | 5.55 ± 0.97 |
| Size (d.nm) | 205 | 205 |

FIG. 7D

| Sample | $P_{50}$ (mm Hg) |
|---|---|
| Mb | 2.00 ± 0.01 |
| PEM-SE | 7.95 ± 0.30 |
| PEM-E | 17.14 ± 0.27 |

FIG. 7E

COMPOSITIONS AND METHODS FOR IMPROVED ENCAPSULATION OF FUNCTIONAL PROTEINS IN POLYMERIC VESICLES

RELATED APPLICATIONS

This application claims the benefit of priority to U.S. Provisional Patent Application Ser. No. 62/187,942, filed on Jul. 2, 2015, the entire content of which is hereby incorporated by reference.

STATEMENT AS TO FEDERALLY SPONSORED RESEARCH

Work on this invention was supported by funds from the National Institute of Health (Study ID#1R43CA159527-01A1 and Study ID#1R43AI096605-01). The United States Government therefore has certain rights in this invention.

BACKGROUND

Natural and synthetic proteins offer an incomparable array of unique biological functions that may be exploited for human therapeutic applications. Their clinical utility, however, is often limited by biochemical instability, poor pharmacologic properties, and potential to induce adverse immunogenicity. Incorporation of biomolecules, such as proteins, in long-circulating vehicles with attached polyethylene glycol (PEG) polymer chains (i.e., PEGylated vehicles), such as nanoparticles, may mitigate such issues. However, the stable encapsulation of large quantities of functional proteins in PEGylated vehicles has proven to be challenging. Conventional encapsulation techniques, which were originally developed for small-molecule drug delivery, require the input of high energies and/or the use of organic solvents for particle formation, and are therefore unsuitable for use with biologically complex and more labile macromolecules.

In particular, examples of conventional encapsulation techniques may include thin-film rehydration, direct-hydration, and electro-formation, which may be used to encapsulate small molecules and proteins with unique biological function into polymersomes generated from poly(ethylene oxide)-block-poly(butadiene) (PEO-b-PBD). For example, methylene blue (mBlue; Mw=319.85 g/mol) may be used as a model small molecule, and myoglobin (Mb; Mw=17,600 Da) may be used a model protein with unique biological function (i.e., oxygen storage). The efficiencies of encapsulating methylene blue and myoglobin into PEO-b-PBD using the thin-film rehydration and direct hydration techniques have been compared. In particular, quantification of the maximum encapsulation of fully functional myoglobin was based on a number of characteristics, using these established techniques. For example, the concentration and the reduction-oxidation reaction ("redox") state of iron in the heme group of myoglobin were respectively measured using inductively coupled plasma optical emission spectroscopy (ICP-OES) and UV-Vis absorption spectroscopy (also referred to as spectrophotometry). The morphologies and stabilities of polymersome-encapsulated myoglobin (PEM) were respectively verified by cryogenic transmission electron microscopy (cryo-TEM) and by dynamic light scattering (DLS). Equilibrium oxygen binding and release at various partial pressures of oxygen were measured using a Hemeox analyzer. While the thin-film rehydration and direct hydration techniques allowed for successful methylene blue encapsulation, encapsulation of myoglobin was uniformly poor. Therefore, improved methods for generating PEM will be beneficial for human therapeutic applications.

SUMMARY

Various embodiments include methods of preparing polymersome-encapsulated functional protein suspensions by thermally blending an amount of a block copolymer with an amount of a low molecular weight polyethylene glycol (PEG) for at least 30 minutes, mixing and cooling a resulting PEG/polymer formulation to room temperature, adding an aliquot of a solution of the functional protein to a sample containing the PEG/polymer formulation, and performing at least three dilution steps in which polymersomes that are generated are progressively saturated with the functional protein. In some embodiments, a ratio of the added aliquot to the PEG/polymer sample is around 0.5:1 to 1.5:1 by volume. In some embodiments, the thermal blending is performed at 90-100° C. In some embodiments, each dilution step includes adding to the sample an additional amount of the solution of the functional protein, mixing a resulting dispersion of the functional protein in the PEG/polymer formulation, and sonicating the resulting dispersion for at least 30 minutes.

In some embodiments, performing the at least three dilution steps includes performing a first, a second, and a third dilution step in a serial fashion. In some embodiments, adding the additional amount of the solution in the first step includes adding a first amount of the solution of the functional protein such that a ratio of the first amount to the PEG/polymer formulation is around 1:1 by volume. In some embodiments, adding the additional amount of the solution in the second step includes adding a second amount of the solution of the functional protein such that a ratio of the second amount to the PEG/polymer formulation is around 2:1 by volume. In some embodiments, adding the additional amount of the solution in the third step includes adding a third amount of the solution of the functional protein such that a ratio of the third amount to the PEG/polymer formulation is around 5:1 by volume. Embodiment methods may also include performing a fourth dilution step in which adding the additional amount of the solution in the fourth step includes adding a fourth amount of the solution of the functional protein such that a ratio of the fourth amount to the PEG/polymer formulation is around 5:1 by volume. Embodiment methods may further also include removing surface-associated protein from polymersomes in the suspension of the polymersome-encapsulated functional protein using proteolysis after the at least three dilution steps. In some embodiments, using proteolysis includes treating the mixed PEG/polymer/protein sample with a 0.4 wt % pronase solution for at least 18 hours at room temperature, and allowing dialysis of the PEG/polymer/protein sample at 4° C. for at least twelve hours.

In some embodiments, the solution of the functional protein may be a 150 mg/mL solution of oxymyoglobin (oxyMb) in phosphate buffered saline (PBS). Embodiment methods may also include preparing the solution of the functional protein by combining a solution of 150 mg/mL metmyoglobin (metMb) in phosphate buffered saline with sufficient amount of 1 wt % sodium dithionite ($Na_2S_2O_4$) to reduce to the metMb to oxyMb. In some embodiments, the block copolymer may be an amphiphilic diblock copolymer. In some embodiments, the amphiphilic diblock copolymer may be poly(ethylene oxide)-block-poly(butadiene) (PEO-b-PBD). In some embodiments, thermally blending an amount of the amphiphilic diblock copolymer with an amount of the low molecular weight PEG for at least 30 minutes includes thermally blending 5-15 mg of poly(ethylene oxide)-block-poly(butadiene) (PEO-b-PBD) with 5-15 mg of 500 kDa PEG (PEG500) for at least one hour. In some embodiments, thermally blending an amount of the amphiphilic diblock copolymer with an amount of the low molecular weight PEG for at least 50 minutes includes thermally blending 10 mg of poly(ethylene oxide)-block-poly(butadiene) (PEO-b-PBD) with 10 mg of 500 kDa PEG (PEG500) for one hour. In some embodiments, thermally blending the amount of the amphiphilic diblock copolymer with the amount of the low molecular weight PEG for at least 30 minutes may include thermally blending 10 mg of poly(ethylene oxide)-block-poly(butadiene) (PEO-b-PBD) with 10 mg of 500 kDa PEG (PEG500) for one hour. In some embodiments, adding the aliquot of the solution of the functional protein may include adding 10 µL of a solution of oxyMb to the sample containing the PEG/polymer formulation. In some embodiments, the thermal blending may be performed at around 95° C.

BRIEF DESCRIPTION OF THE DRAWINGS

The accompanying drawings, which are incorporated herein and constitute part of this specification, illustrate exemplary embodiments, and together with the descriptions of various embodiments, serve to explain the features herein.

FIG. 1 is a table of results from encapsulating a variety of proteins using existing techniques.

FIG. 2 is a table of properties for two poly(ethylene oxide)-block-poly(butadiene) (i.e., PEO-b-PBD) diblock copolymers and their polymersome formulations used for small molecule and protein encapsulation.

FIG. 4 is a table showing encapsulation results from using the progressive saturation protocol and OB29 polymersomes to encapsulate a range of proteins according to the various embodiments.

FIG. 7A is a schematic representation of the progressive saturation protocol for forming polymersome-encapsulated myoglobin in various embodiments.

FIGS. 7B and 7C are graphs illustrating results from encapsulation of myoglobin into polymersomes formed from a particular PEO-b-PBD formulation using the progressive saturation protocol of FIG. 7A.

FIG. 7D is a table summarizing the results shown in FIGS. 7B and 7C.

FIG. 7E is a table showing the partial pressure of oxygen required to achieve 50% saturation ($P_{50}$) obtained from $O_2$ equilibrium curves for of free myoglobin and for polymersome-encapsulated myoglobin, prior to proteolysis and after pronase treatment, that was prepared by progressive saturation.

DETAILED DESCRIPTION

Figure 3A:
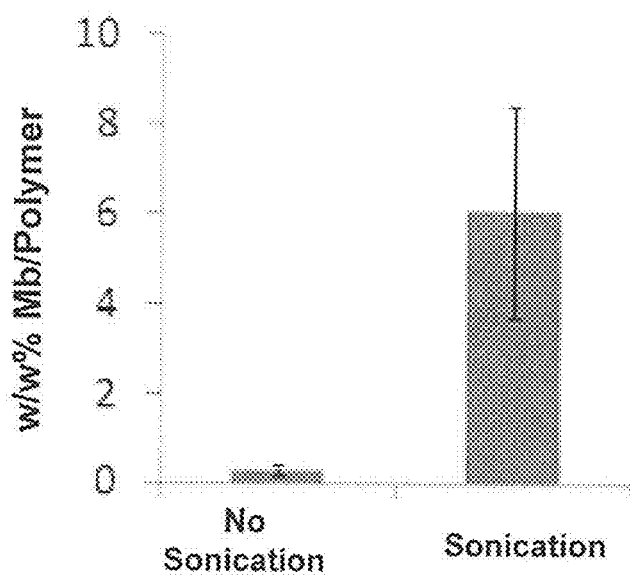
FIGS. 3A and 3B are graphs showing results from optimization of various steps in the direct hydration protocol to improve encapsulation of myoglobin in polymersomes of a particular PEO-b-PBD formulation.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The various embodiments include improved methods for generating PEM, which may include identifying the key parameters of the thin-film rehydration and direct hydration protocols that prevent efficient uptake and/or compromise protein function, and performing iterative optimization of such key parameters. As a result, the various embodiments provide a generalizable technique that enables the encapsulation of increased quantities of functional proteins within neutrally charged and fully PEGylated polymer vesicles. That is, the various embodiments include a new "progressive saturation" method for encapsulating myoglobin in polymersomes.

Nanoparticle vehicles may overcome many challenges associated with the delivery of functional proteins to enable the clinical development of diverse macromolecular pharmaceuticals. Nanoparticle vehicles may include, for example, liposomes (i.e., self-assembled vesicles of natural phospholipids) and polymersomes (i.e., self-assembled polymer vesicles of block copolymers), as well as micelles, perfluorocarbon emulsions, and others. To that end, polymersomes, have advantageous properties as compared to conventional liposomes, as liposomes typically have high membrane permeability and low stability in vivo. There have been, however, few comparative studies to establish and validated a single, scalable and generalized strategy for encapsulating large amounts of protein in neutrally charged and/or PEGylated polymersomes. By optimizing and combining different steps from various liposome-based encapsulation methods, the various embodiments provide a new progressive saturation technique that allows improved encapsulation of functional proteins in nanoscale polymer vesicles. The various embodiments demonstrate a tradeoff between the degree of polymersome loading (i.e., weight percentage of protein-to-polymer) and the encapsulation efficiency of protein (with respect to the initial quantity that was employed for polymersome formation) that may be achieved. Moreover, in the various embodiments, a proteolysis step accurately quantifies the amounts of both encapsulated protein (i.e., the desired outcome) as well as surface associated (i.e., non-specifically bound) product that may be obtained in polymersome suspensions formed by the progressive saturation protocol. While there are some reports of large amounts of protein loading within polymersomes at high efficiencies using existing liposome encapsulation techniques, such reports do not involve differentiating between encapsulated and surface-associated protein. Therefore, the progressive saturation technique in the various embodiments may provide a more robust, scalable, and generalizable strategy for encapsulation of proteins in fully PEGylated and neutrally charged polymersomes in quantities and at efficiencies that may enable further translational development.

Selective and potent modulation of protein function in mammalian cells is the principal activity of most molecular therapeutics, where the vast majority of available agents are organic small molecules (less than or equal to 800 Da in size). Recent studies suggest, however, that only a small percentage of the human proteome is susceptible to small molecule-based therapy. Moreover, the functional diversity of proteins that are successfully targeted by small molecules remains very low. That is, around 40% of all prescription drugs target a single class of proteins, namely the G-protein coupled receptors. However, use of small-molecule therapy is limited since small drug molecules are intrinsically unable to cope with the extended contact surfaces found at many biologically important interfaces.

Biomacromolecules such as proteins have recently shown significant clinical utility, in large part due to their ability to overcome these significant limitations associated with traditional small molecule therapies. When compared to the interaction of a small-molecule with its biological target, macromolecular therapeutics have higher folding energies (typically around 7-20 kcal/mol) that allow for the adoption of larger and more precise three-dimensional configurations, which are often required for efficient binding and/or control of complex biological function. As such, macromolecules may achieve superior binding selectivity and more potent on-target activity. Currently, a small number of macromolecular therapies in use, including the approximately 200 protein drugs available worldwide, have demonstrated a high potential as new leads in drug development. Nevertheless, several barriers have hindered the ready development of macromolecules as human therapeutics, including: (i) the difficulty and/or expense of commercial scale production, (ii) biochemical instability that occurs in pathophysiologic environments or with prolonged storage, (iii) short circulatory half-lives and large steric hindrance that prevent effective tissue penetration, and (iv) risks associated with their potential to promote severe adverse effects, such as the induction of anti-idiotypic antibodies and/or immune complex formation. To overcome some of these limitations, most pharmaceutical compounds either employ biocompatible polymers (e.g., polyethylene glycol (PEG) or hyaluronic acid) or liposomes (i.e., lipid based vesicles) for protein complexation and in vivo delivery.

Synthetic nanoparticles may exhibit superior properties to enhance drug delivery when compared to more conventional formulations. In particular, among the classes of nanoparticles, polymersomes (i.e., self-assembled polymer vesicles comprised of amphiphilic block copolymers) may provide a beneficial nanoscale delivery platform. While lipid-based vesicles (i.e., liposomes) have been extensively utilized in biomedical research, there are material limitations inherent to these phospholipid-based drug delivery vehicles, including compromised suspension stability, premature drug release, and limited product shelf-life. In contrast, polymersomes are formed from higher molecular weight amphiphilic block copolymers that impart a broad and tunable range of carrier properties. For example, polymersomes enable: (i) facile and stable loading of diverse therapeutic payloads through non-covalent interactions, (ii) mechanical stability that is 5 to 50 times greater than that of liposomes or micellar structures constructed from similar molecular weight copolymers, (iii) economic and large scale production that removes the need for costly post-manufacturing purification, and (iv) diversity in biochemical properties, which are imparted by their construction from a variety of copolymer compositions. Such properties may include fully PEGylated surfaces and tunable in vivo circulation times, site-specific targeting, environmental responsiveness, and complete biodegradation.

The incorporation of proteins into nanoparticles may enhance their pharmacologic performance and improve their on-target activity. Methods that have been developed for encapsulating proteins into nanoparticles have utilized electrostatic interactions to incorporate a handful of highly anionic proteins, or chemical or genetic modification of the original protein for efficient and reproducible nanoparticle formation. Examples of such method include thin-film rehydration (i.e., rehydration of dried polymer), which results in low yields of polymersome-encapsulated protein. Another example method is direct hydration, the use of which is generally limited to small-scale preparations (e.g., less than one mL). Another example method is electro-formation, which provides useful results for only a limited number of proteins (i.e., highly charged proteins). Another example method is hollow-fiber extrusion, which involves extrusion of preformed vesicles in the presence of protein solution. While the hollow-fiber extrusion technique has been used for large-scale preparations of liposome-encapsulated protein, elevated temperatures and pressures are required for polymersome formation, which has limited its widespread applicability.

Existing techniques require the input of thermal, electric, ultrasonic, or mechanical energy for particle formation, or alternatively the use of organic cosolvents, which may damage the structure and/or function of the protein, making encapsulation more challenging and limited in utility. Therefore, in various encapsulation techniques, a need exists for a generalized method that enables the incorporation of large quantities of native protein in neutrally charged and/or PEGylated nanoparticles.

While adoption of various liposome encapsulation techniques has enabled facile incorporation of small molecules within polymersomes, these methods cannot directly be applied for scalable encapsulation of the functional proteins. Often, there is a trade-off in the maximum concentration of the aqueous protein that may be encapsulated (i.e., mg protein/mL solution), the final loading ratio of protein-to-polymer that comprises the polymersome structure (i.e., w/w % protein/polymer), and/or the protein encapsulation efficiency (i.e., the percentage of the initial protein suspension that is retained). Further, the value of each of these parameters is highly dependent on the nature of the protein, the exact block copolymer formulation, and the encapsulation method that is utilized. For example, the table in FIG. 1 shows existing results from encapsulation of various proteins into polymersomes. The various embodiments provide an alternative, optimized and reproducible method to efficiently encapsulate increased quantities of functional proteins in polymersomes. The newly developed "progressive saturation" technique of the various embodiments is readily scalable, highly reproducible, and generalizable for producing increased quantities of polymersome-encapsulated protein that may enable new and diverse biomedical applications.

In various embodiments, PEO-b-PBD copolymers are used to form polymersomes that possess fully PEGylated surfaces. Such surfaces, being uncharged and nondegradable; provide an ideal system for ensuring vesicle integrity and minimizing unwanted protein interactions or modifications. Two different molecular weight PEO-b-PBD polymers, "OB18" diblock copolymer and "OB29" diblock copolymer, are employed to determine the generalizability of the results as they pertain to polymersomes of different minimal sizes, PEG lengths, and membrane core thicknesses. FIG. 2 provides a table showing a comparison of various properties of OB18 and OB29. Methylene blue (mBlue; Mw=319.85 g/mol), which is highly stable in aqueous suspension and has a strong near-infrared absorbance enabling ready spectrophotometric detection, is used as a model small molecule to establish various baseline parameters for encapsulation using existing methods. Such baseline parameters include aqueous suspension concentration, final weight percentage, and encapsulation efficiency. Myoglobin (Mb; Mw=17,600 Da), which has a size and thermal stability (i.e., denaturation above 60° C.) comparable to other small proteins with therapeutic potential, was used as a model protein. Myoglobin also has a strong ultraviolet (UV) absorbance that enables ready identification of its functional status, as determined by the redox state of its iron-containing heme group. Myoglobin has additionally been employed in other studies, enabling comparisons of results to other encapsulations using existing techniques, as discussed above with respect to FIG. 1. Methylene blue is easily encapsulated in PEO-b-PBD polymersomes formed by thin-film rehydration at elevated temperatures, yielding final weight ratios of mBlue-to-polymer of 4.1 and 5.0 w/w % when formed at 40 and 60° C., respectively. However, similar conditions only led to myoglobin degradation.

When vesicles are formed by thin-film rehydration, as the film of dry copolymer is hydrated, lamellae (aka sponge-like structures) are first formed as the hydrophilic blocks in the film swell. Further swelling leads to transformation into hexagonally packed vesicles and finally into fully dispersed polymersomes. When thin-film rehydration is attempted in solutions of soluble small molecules (or proteins), these water-soluble species adsorb to the surfaces of the budding lamellae, which subsequently adopt a spontaneous (or preferred) curvature. During formation, these membranes preferentially bend away from the aqueous compartment that contains the higher concentration of adsorbing species, thereby excluding the water-soluble agents from vesicle encapsulation. Ultimately, the input of energy can overcome this spontaneous surface tension in order to promote vesicle encapsulation. The amount of energy that is required scales with the size of the adsorbed molecule and the membrane thickness of the vesicle. Thus, while it is easy to disrupt liposomes and enable effective small molecule and protein loading by thin-film rehydration by the input of thermal (and/or sonic) energy, such input is only enables effective encapsulation of small molecules into polymersome suspensions. In the direct hydration method, which was developed as a hybrid of solvent dispersion and homopolymer addition, the hydrophilic polymer PEG500 dimethyl ether (DME) is used to disrupt the interactions of hydrophobic chains in the forming polymer lamellae. With subsequent additions of aqueous solution, self-assembly of vesicles from budding lamellae that have dispersed protein is promoted and results in improvements in aqueous encapsulation; encapsulation efficiencies as high as 37% have been observed. Using direct hydration at 23° C., polymersome-encapsulated myoglobin suspensions may have encapsulation efficiencies greater than 10%, with the encapsulated myoglobin species exhibiting good suspension properties and the characteristic absorption spectra of intact protein. The final loading of myoglobin in these polymersome-encapsulated suspensions, however, was found to be only around 0.3 w/w % Mb/polymer. Upon addition of a protease solution to induce proteolysis of all surface associated (i.e., non-specifically bound) protein, the final Mb composition of PEM suspensions was found to be even lower—that is, less than 0.1 w/w % Mb/polymer. For translational therapeutic applications, the loading of therapeutic proteins within the aqueous cavities of polymersome vehicles is ultimately the metric that must be maximized in order to minimize the amount of associated carrier that is introduced to a subject. Therefore, such encapsulation using standard direct hydration is insufficient.

In various embodiments a progressive saturation protocol provides for efficient generation of PEM suspensions. The generalizability of progressive saturation for protein encapsulation is further established by utilizing a variety of different proteins, ranging from 17-450 kDa, yielding nanoscale polymersomes in quantities that may enable preclinical investigations of many novel therapeutic compositions. In particular, a difference between the progressive saturation method and direct hydration may involve adding five subsequent volumes of the functional protein solution to dilute the PEG/polymer mixture in lieu of additional dilutions with phosphate buffered saline (PBS).

Specifically, the progressive saturation method of the various embodiments involves heating 10 mg of polymer and 10 mg of PEG at around 95° C. for around 1 h. The sample mixture may be centrifuged and cooled to room temperature. A metmyoglobin (metMb) solution (e.g., 150 mg/mL in PBS) may be reduced to oxymyoglobin (oxyMb) with sodium dithionite ($Na_2S_2O_4$) (e.g., 1 wt %). From the resulting oxyMb solution, a portion (i.e., aliquot) may be added to the sample mixture at a ratio of 1:1 by volume, and mixed thoroughly followed by sonication at room temperature for around 30 min. In particular, the aliquot may be 10 µL of the oxyMb solution. The sample mixture may be further diluted with a number of dilution steps. Specifically, each dilution step may involve addition of a volume of the oxyMb solution (e.g., 150 mg/mL in PBS), followed by thorough mixing and sonication at room temperature for around 30 minutes. The volumes of oxyMb solution used in the dilution steps may be amounts in which ratios of the oxyMb solution to the original sample mixture are 1:1, 2:1, 5:1, and 5:1 by volume 10 µL, followed by 20, 50 and 100 µL. After the dilution steps, the resulting sample may be sonicated for an additional 30 min at room temperature, followed by dialysis for at least 30 h at around 4° C., employing a 1000 kDa molecular weight cutoff membrane. Surface associated myoglobin may be removed by proteolysis via treatment with 0.4 wt % pronase solution, followed by dialysis for at least 12 h at around 4° C. (e.g., molecular weight cutoff of 1000 kDa). In various embodiments, myoglobin encapsulation of the resulting polymersome suspension may be measured before and after proteolysis. Specifically, concentration of myoglobin may be measured using inductively coupled plasma optical emission spectroscopy (ICP-OES), while redox states of iron in the heme group of myoglobin may be quantified using UV-Vis absorption spectroscopy.

These progressive saturation steps provided favorable results for encapsulating myoglobin in OB18 polymersomes, as shown in FIGS. 3A-3E. For example, FIG. 3A shows the final weight percentage of Mb-to-polymer (i.e., w/w % Mb/polymer) in polymersome-encapsulated myoglobin obtained when no sonication was used (as in conventional techniques) and by using sonication, according to the progressive saturation protocol (i.e., for around 30 min at room temperature after each dilution step). A shown in FIG. 3A, a final weight percentage of Mb-to-polymer of around 6 (i.e., w/w % Mb/polymer) may be an achieved result from polymersome-encapsulated myoglobin created by a protocol that includes such sonication. Therefore, sonicating the sample for around 30 min at room temperature after each dilution step may increase encapsulation efficiency by more than 30 times based on the final weight percentage resulting from polymersome-encapsulated myoglobin generated via direct hydration.

Figure 3B:
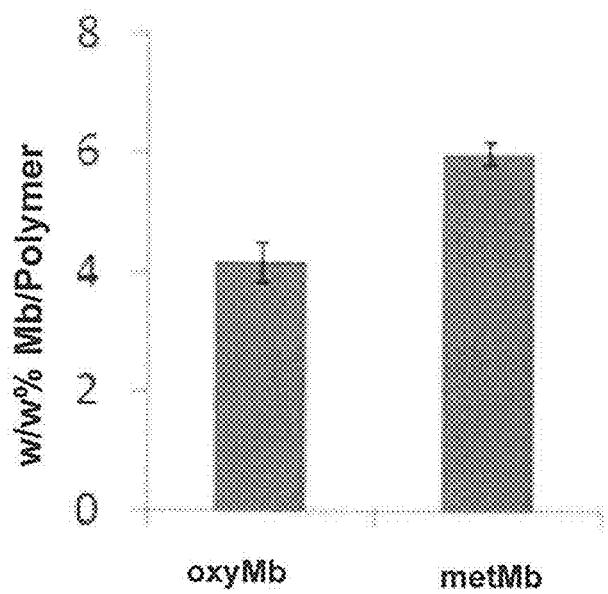
Figure 3C:
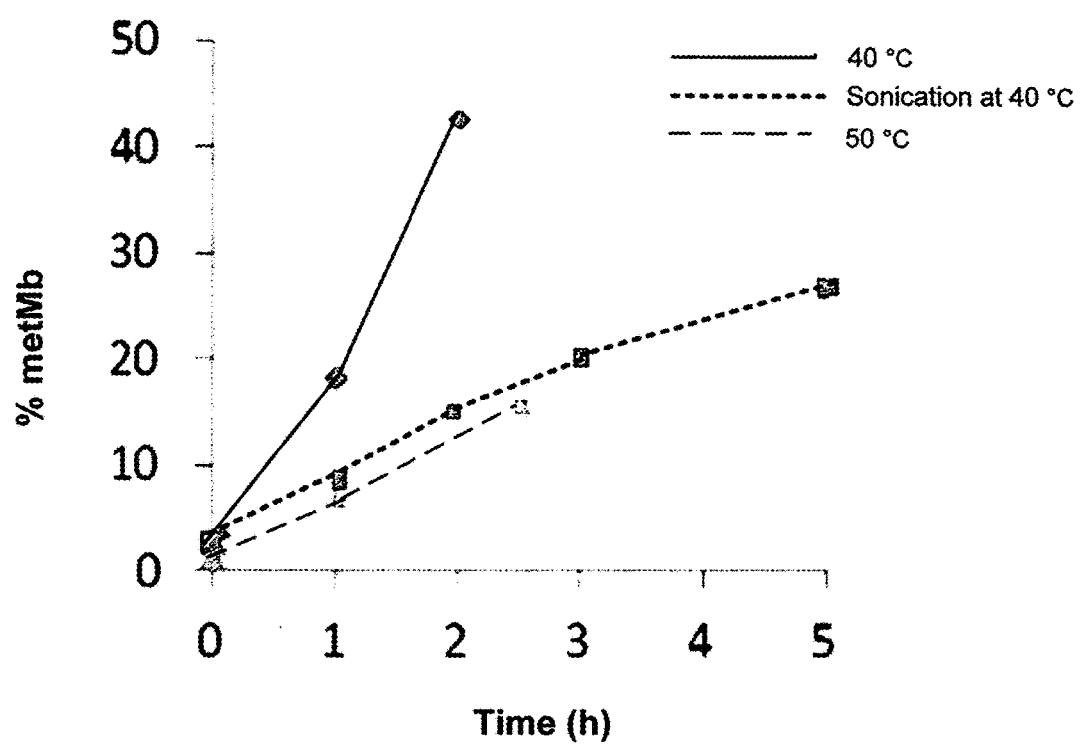
FIGS. 3C and 3D are graphs showing the rate of myoglobin oxidation and the loss of surface-associated myoglobin from proteolysis as functions of time.
Figure 3D:
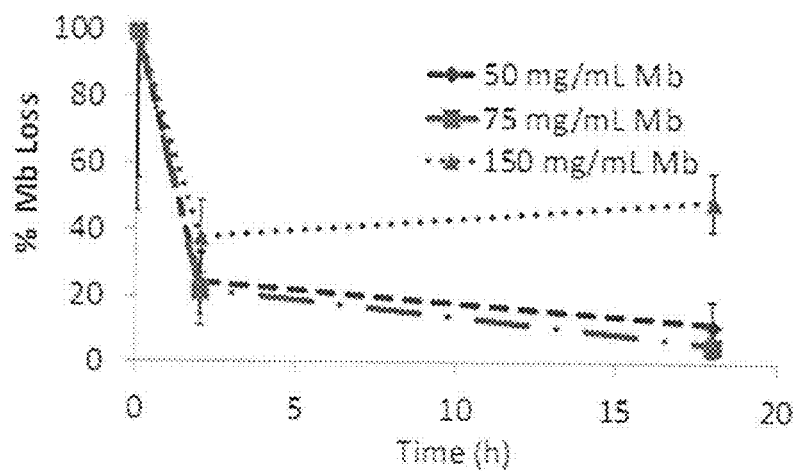
Figure 3E:
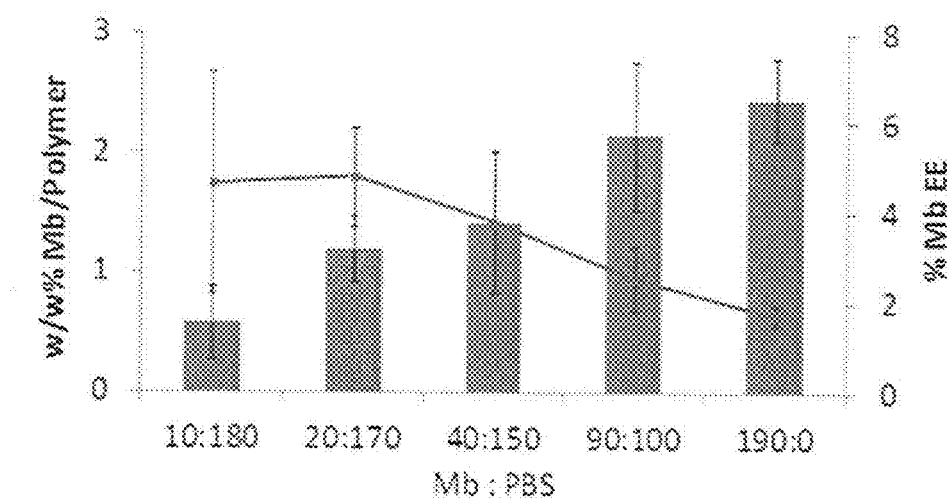
FIG. 3E is a graph showing final weight percentage compared to encapsulation efficiency of myoglobin using various ratios of myoglobin to phosphate buffered saline solution.

FIG. 3B shows the final weight percentage of Mb-to-polymer (i.e., w/w % Mb/polymer) in polymersome-encapsulated myoglobin obtained using a metmyoglobin solution (as in conventional techniques) and by using oxyMb as in the progressive saturation technique. FIG. 3C shows the rate of myoglobin oxidation (expressed as a percentage of metMb formed over time) as a function of myoglobin exposure to different solution conditions. FIG. 3D shows the amount of surface-associated Mb removed (% Mb loss) as a function of proteolysis time for various oxyMb volumes. FIG. 3E shows the final weight percentage of Mb-to-polymer (i.e., w/w % Mb/polymer) compared to encapsulation efficiency (% Mb EE) in polymersome-encapsulated myoglobin generated using various ratios for the volumes of oxyMb solution to PBS used in the dilution steps. In particular, the samples in FIG. 3E were proteolyzed for 18 h to remove surface-associated myoglobin, and quantified using UV-Vis absorption spectroscopy.

Therefore, the final Mb-to-polymer weight ratios that were obtained in generating polymersome-encapsulated myoglobin using progressive saturation according to various embodiments (i.e., 4-6 w/w % Mb/polymer) may be significantly improved compared to polymersome-encapsulated myoglobin generated using the direct hydration protocol (i.e., 0.1-0.3 w/w % Mb/polymer). Without wishing to be bound to a particular theory, the loading capacity achieved using progressive saturation steps may be due to incomplete polymersome formation during the initial dilution step, and further encapsulation being accomplished with each subsequent addition of protein solution.

Developing the progressive saturation protocol included optimizing and combining various steps from multiple liposome formation methods. Factors influencing the final concentrations of myoglobin, the relative loading levels that could be achieved within the OB18 polymersome carrier (i.e., w/w % protein/polymer), and the efficiency of myoglobin encapsulation were systematically evaluated. Factors such as the molecular weight of the polymer, the oxidation state and concentration of the protein, the pH and nature of the buffered solution, the exact polymer hydration conditions (i.e., time, temperature, and blending technique), the number and duration of sonication steps, and the addition or avoidance of freeze-thaw cycles all had effects on the concentration and the fidelity of the final polymersome-encapsulated protein product.

Further, compared to polymersome-encapsulated myoglobin created using existing techniques, polymersome-encapsulated myoglobin created by progressive saturation also exhibits an increase in the final concentrations of Mb. For example, the final concentration of Mb in polymersome-encapsulated myoglobin generated via direct hydration is less than around 0.5 mg/ML in solution, while that of polymersome-encapsulated myoglobin generated via progressive saturation in the various embodiments may be greater than around 2.0 mg/mL in solution.

Using cryo-TEM to verify vesicle morphologies, suspensions of polymersome-encapsulated myoglobin developed using progressive saturation showed no signs of aggregate formation when maintained at 4° C., 23° C., and 37° C. for longer than one month. The progressive saturation technique may be further utilized for the successful encapsulation of a variety of other proteins ranging in size from 17 to 450 kDa, within PEO-b-PBD polymersomes.

Without wishing to be bound to a particular theory, there may be a direct tradeoff between Mb encapsulation efficiency and the final weight ratios of Mb-to-polymer that could be achieved based on the concentration of free Mb that was used for each addition step. Aqueous encapsulation of protein is preferred to surface-associated protein in order to assure that the final product meets the objectives for utilizing a polymersome delivery vehicle—that is, to improve biochemical stability, to increase circulatory half-life, to minimize adverse side effects, and to achieve controlled release of the associated protein. The various embodiment techniques may be employed using different proteins that vary over a large range of molecular weights and sizes, including those associated with therapeutically relevant antibodies and enzymes. For example, the progressive saturation technique may be utilized to encapsulate myoglobin in a PEO-b-PBD-based polymersome system comprised of the OB29 diblock copolymer. In various embodiments, the progressive saturation technique may be utilized to encapsulate any of a number of other proteins, including, but not limited to, antibodies (e.g., immunoglobulin G (IgG) and functional enzymes (e.g., catalase).

As described above with respect to FIG. 2, when compared to the OB18 diblock copolymer, the OB29 diblock copolymer has a smaller molecular weight and generates polymersomes with a shorter PEG brush border (1.3 vs. 3.9 kDa), thinner bilayer membrane (9.6 nm vs. 14.8 nm), and smaller average hydrodynamic diameter (130 vs. 200 nm). In various embodiments, using progressive saturation to encapsulate myoglobin in OB29 polymersomes provides similar results to those from OB18 polymersomes. In various embodiments, progressive saturation technique may be applied using any PEG-based polymersome-forming block copolymer, including any amphiphilic polymer comprised of PEG and a hydrophobic block that is a biodegradable polymer (e.g., a biodegradable polyester, poly(amide), poly (peptide), poly(nucleic acid), etc.). Examples of biodegradable polyesters that may form the hydrophobic block include, but are not limited to, poly(lactic acid), poly(glycolic acid), poly(lactic-co-glycolic acid), poly(caprolactone), poly(methyl caprolactone), poly(hydroxybutyrate), poly(hydroxyvalerate), poly(hdyroxyhexanoate), poly(hydroxyoxtanoate), and poly(trimethylene carbonate).

The generalizability of the progressive saturation technique is further demonstrated by analogous results from encapsulation of several larger proteins using OB29 polymersomes. FIG. 4 shows encapsulation results from using the progressive saturation protocol and OB29 polymersomes to encapsulate myoglobin, hemoglobin (Hb) (64 kDa), bovine serum albumin (BSA) (66 kDa), IgG (150 kDa), catalase (250 kDa), fibrinogen (340 kDa), and apoferritin (450 kDa).

The invention is intended to be illustrated but not limited by the following examples.

EXPERIMENTAL

Figure 5A:
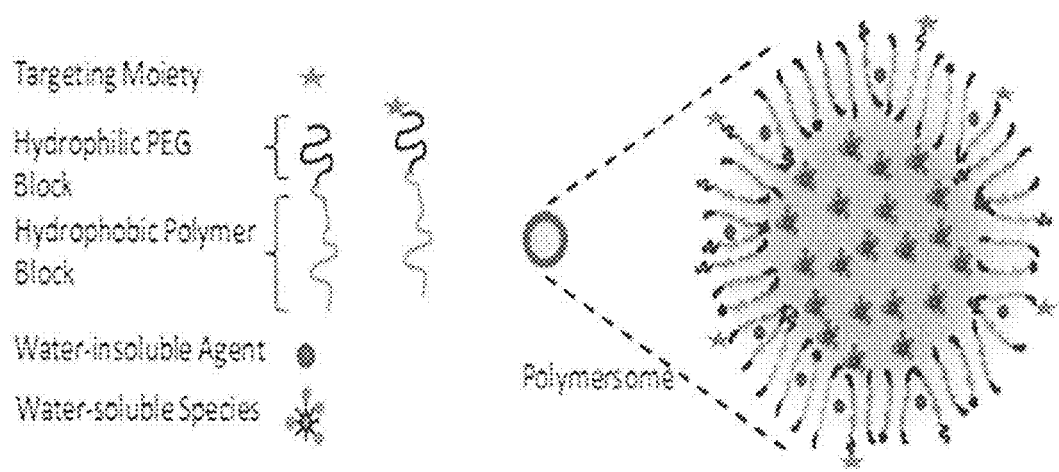
FIG. 5A is a schematic representation of components of polymersomes prepared according to the various embodiments.
Figure 5B:
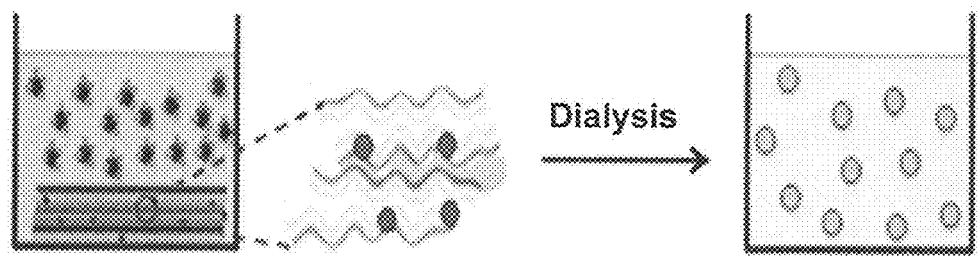
FIG. 5B is schematic representation of the existing thin-film rehydration protocol for forming polymersome-encapsulated myoglobin.
Figure 5C:
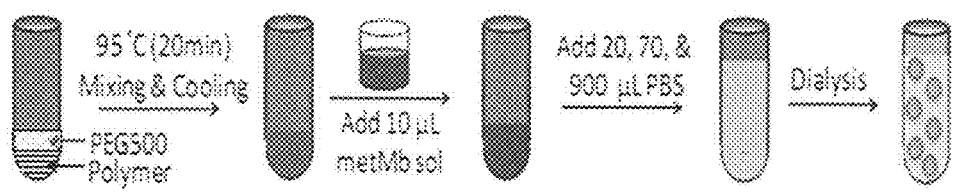
FIG. 5C is a schematic representation of the existing direct hydration protocol for forming polymersome-encapsulated myoglobin.

Comparative and quantitative studies were performed in order to establish a generalizable method for producing scalable quantities of neutrally-charge and fully PEGylated polymersomes that encapsulate functional protein. Differences in small molecule and protein encapsulation were examined by employing polymersome formulations comprised of OB18 and OB29 diblock copolymers. As described above with respect to FIG. 2, these two PEO-b-PBD polymers and the polymersomes formed therefrom differ with respect to molecular weight and, ultimately, vesicle membrane thicknesses. Methylene blue (mBlue; Mw=319.85 g/mol) was used as a model small molecule and myoglobin (Mb; Mw=17,600 Da) as a model protein with unique biological function (i.e., oxygen storage and release). FIG. 5A shows a representation of polymersomes made of amphiphilic diblock copolymers, as well as water-insoluble agents and water-soluble species that may be encapsulated in or attached to polymersomes. For example, conventional vesicle formation techniques that were employed to incorporate water-soluble agents within PEO-b-PBD polymersomes included thin-film rehydration and direct hydration, protocols for which are shown in FIGS. 5B and 5C, respectively. The encapsulations of methylene blue and myoglobin in PEO-b-PBD polymersomes generated by each of the thin-film rehydration and direct hydration methods were compared. In order to quantify the encapsulation of fully functional protein capable of oxygen binding, the iron concentration in polymersome-encapsulated myoglobin was measured by ICP-OES, and the redox states of iron in the heme group of myoglobin measured by UV-Vis absorption spectroscopy.

Compared to PEM created using existing techniques, PEM created by progressive saturation exhibit an increase in the final concentrations of Mb (e.g., from less than around 0.5 mg/mL in solution to greater than around 2.0 mg/mL in solution), and an increase in the final weight ratio of Mb to polymer that could be reproducible obtained (from less than 1 w/w % Mb/polymer to greater than around 3-4 w/w % Mb/polymer). Further, PEM created by progressive saturation show an increase in the overall efficiency of protein encapsulation (from less than around 5% to greater than around 90%) in the PEM suspensions. Using cryo-TEM to verify vesicle morphologies, suspensions of PEM developed using progressive saturation display no signs of aggregate formation for longer than one month at 4° C., 23° C., and 37° C.

Materials

PEO(3900)-b-PBD(6500) (OB18) and PEO(1300)-b-PBD(2500) (OB29) were purchased from Polymer Source (Dorval, Quebec, Canada). Horse skeletal muscle Mb, bovine blood hemoglobin (Hb), bovine serum albumin (BSA), catalase (C), fibrinogen (F), sodium hydrosulfite, poly(ethylene glycol) dimethyl ether (PEG; Mn=~500), protease from *Streptomyces griseus* ("pronase"), and dichloromethane (DCM) were purchased from Sigma-Aldrich (St. Louis, USA). Horse spleen apoferritin (aFr) was purchased from Alfa Aesar (Ward Hill, USA) Immunoglobulin G (IgG) was purchased from LEE Biosolutions (St. Louis, USA). Dialysis tubing and vials were purchased from Spectrum Laboratories (Rancho Dominguez, USA). Sodium chloride, potassium chloride, sodium phosphate dibasic, potassium phosphate monobasic, mBlue, and Triton X-100 were purchased from Fisher Scientific (Suwanee, USA). All chemicals were of reagent grade unless otherwise stated.

The particle sizes were measured using Delsa™ Nano, a dynamic light scattering (DLS) instrument (Beckman Coulter, Indianapolis, USA). Mb and mBlue concentrations were determined by absorption spectroscopy using a Genesys™ 10 S UV-Vis spectrophotometer (Thermo Scientific, Suwanee, USA). The concentrations of all proteins in polymersome suspension were further measured using a Micro BCA Protein Assay Kit, utilizing UV-Vis spectrophotometry and by following the manufacturer's protocols (Pierce Biotechnology, Inc; Rockford, Ill., USA). Iron concentrations in polymersome-encapsulated Mb suspensions were determined using a Vista-PRO CCD ICP-OES (Varian, USA). Oxygen equilibrium binding was studied using a Hemox™-Analyzer (TCS Scientific Corp, New Hope, Pa., USA). Electro-formation was performed using Gene Pulser (Bio-Rad, Hercultes, Calif., USA).

Methods

Thin-Film Rehydration Method 10 mg of OB18 polymer was dissolved in 200 μL of DCM. The polymer solution was deposited on Teflon wafers (15 mm×15 mm) that were subsequently dried for 30 min at room temperature (RT). The films were further kept under vacuum overnight at RT to ensure DCM evaporation. For methylene blue encapsulation, polymer films were then hydrated with methylene blue solution (21 mg/mL) in phosphate buffered saline (PBS; 10 mM, pH 7.4) for 24-48 h at 23, 40 or 60° C. The samples were sonicated for 30 min at room temperature, followed by (×10) freeze-thaw cycles using liquid nitrogen. The samples were dialyzed (MW cutoff=100 kDa) for 30 h at RT. For myoglobin encapsulation, polymer films were hydrated with myoglobin solution (150 mg/mL) in PBS (10 mM, pH 7.4) for 60 h at 23, 40, and 60° C. The samples were then sonicated for 30 min at RT followed by dialysis (MW cutoff=1000 kDa) for 30 h at 4° C.

Direct Hydration Method 10 mg of OB18 and 10 mg of PEG were heated in a 1.5 mL centrifuge tube for 20 min at 95° C. The samples were mixed and cooled to room temperature, followed by the addition of 10 μL of methylene blue solution (21 mg/mL) or myoglobin solution (150 mg/mL) in PBS (10 mM, pH 7.4). The samples were then diluted with 20, 70, and 900 μL of PBS and well mixed after each addition/dilution (via vortexing). The samples were then dialyzed for 30 h at room temperature or at 4° C. (molecular weight cutoff of 1000 kDa) to remove unencapsulated methylene blue or myoglobin, respectively.

Quantification of mBlue/Mb

The amounts of methylene blue or myoglobin that were encapsulated in purified polymersome suspensions were determined by measuring solution absorbance at 665 nm (mBlue) or at 410 nm (Mb), using a UV-Vis spectrophotometer. Calibration curves for methylene blue and myoglobin were developed using serial dilutions of known concentrations. To measure the iron content in polymersome-encapsulated myoglobin suspensions (as a corroboration of myoglobin concentration in that sample), 5-10% (v/v) of Triton X-100 was added, the mixture was digested by heating in aqua regia for 3 h at 98° C., and was subsequently diluted with deionized water. ICP-OES was performed on experimental samples and their iron content was determined in comparison to this standard calibration curve. The concentrations of myoglobin (as calculated by UV-Vis absorbance spectroscopy) were compared to those obtained via ICP-OES or via the Micro BCA Assay (secondary UV-Vis method) for each suspension. Loading of aqueous encapsulants in the polymersomes was quantified and expressed as the final weight percentages of encapsulant-to-polymer that comprised the vesicles in suspension (e.g., w/w % Mb/polymer).

Quantification of metMb

The amount of metmyoglobin (metMb, i.e., oxidized Mb with a Fe(III)-heme group) in polymersome suspensions was quantified using a modified UV-Vis absorption protocol that was previously established for the measurement of cyanomethemoglobin levels. In brief, the absorbance of myoglobin was measured at 630 nm ($L_1$) against a blank reference (deionized water). One drop of KCN solution (1 part 10% KCN and 1 part 50 mM phosphate, pH 7.6) was added and mixed with the treated myoglobin samples. This reaction step was necessary to convert metMb to cyanometmyoglobin (cyanoMb), which does not absorb at 630 nm. After 2 min, the absorbance was measured at 630 nm ($L_2$) against the deionized water, which served as the blank reference. The concentration of metMb was determined using Equation 1:

$$[metMB]\ (mM) = \frac{L_1 - L_2}{1 \times E} \times D_1, \quad \text{(Eq. 1)}$$

where E=3.7 (cm×mM)$^{-1}$ and is the extinction coefficient of metMb at 630 nm, and $D_1$ is the dilution factor in this experiment (cuvette length=1 cm).

To determine the concentration of myoglobin, one drop of 20% $K_3(Fe(CN)_6)$ was added and mixed with the treated myoglobin sample. The solution was allowed to react for 2 min and an additional drop of 10% KCN was added and mixed. The absorbance of the sample was then measured at 540 nm ($L_3$). The concentration of total Mb was determined using Equation 2:

$$[total\ Mb]\ (mM) = \frac{L_3}{1 \times E} \times D_2, \quad \text{(Eq. 2)}$$

where E=11.3 (cm×mM)$^{-1}$ and is the extinction coefficient for cyanometMb at 540 nm; $D_2$ is the dilution factor (cuvette length=1 cm).

The percentage of metMb in the original solution was determined using Equation 3:

$$[metMB](\%) = \frac{[metMB]}{[metMB] + [total\ Mb]} \times 100. \quad \text{(Eq. 3)}$$

Structural Characterization of Polymersomes

Polymersome suspensions were diluted in PBS solution and their hydrodynamic diameters were measured by DLS using a standard 1.5 mL semi-micro Plastibrand polystyrene cuvette (VWR, Atlanta, USA). The morphologies of blank polymersomes and polymersome-encapsulated myoglobin were visualized by cryo-TEM (JEOL 2100F, USA). In brief, polymersome samples were suspended in a microperforated grid, rapidly vitrified using liquid ethane (−183° C.), and loaded onto a cryogenic sample holder for cryo-TEM imaging at 200 kV.

Figure 6A:
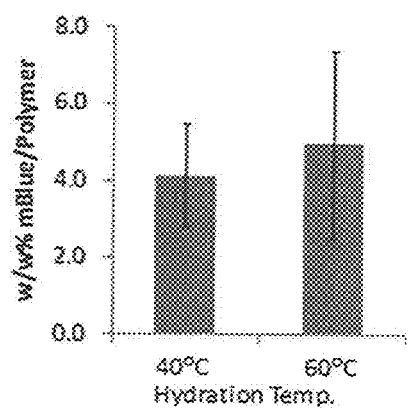
FIGS. 6A and 6B are graphs showing results from encapsulation of methylene blue into polymersomes formed from a particular PEO-b-PBD formulation using existing protocols.

Encapsulation of mBlue and Mb in Polymersome Suspensions Using Conventional Methods To establish a baseline for comparisons of small molecule and protein encapsulation in polymersome suspensions, the final concentrations, weight percentages (i.e., weight of encapsulated agent compared to the weight of the polymer that comprises the nanoparticle), and efficiencies of encapsulation for methylene blue were determined with OB18 polymersomes formed by the thin-film rehydration technique. FIG. 6A shows the weight percentage results of the final polymersome composition for encapsulation of methylene blue at 40° C. (i.e., 4.1 w/w % mBlue/polymer) and 60° C. (i.e., 5.0 w/w % mBlue/polymer). When thin-film rehydration was attempted at room temperature (i.e., 23° C.), the encapsulation of methylene blue was found to be negligible (results not shown), possibly due to the observation that the polymer films did not swell after 48-72 h of hydration. PEO-b-PBD-based polymersomes require the input of energy for vesicle formation, which is usually supported by using elevated temperatures (e.g., greater than 45° C.).

Figure 6B:
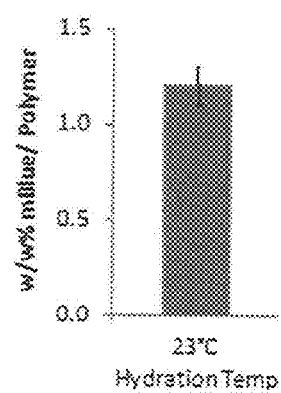

To improve the efficiency of encapsulation at lower temperatures, which would be necessary when employing labile proteins, encapsulation of mBlue was also studied by the direct hydration method. FIG. 6B shows the final weight percentage of mBlue-to-polymer in polymersome suspensions created using direct hydration at 23° C. (i.e., 1.2 w/w % mBlue/polymer).

Figure 6C:
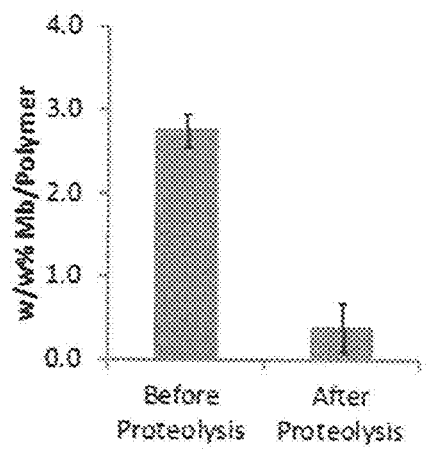
FIGS. 6C and 6D are graphs showing results from encapsulation of myoglobin into polymersomes formed from a particular PEO-b-PBD formulation using existing protocols.

Next, polymersome-encapsulated myoglobin suspensions formed at 23° C. by thin-film rehydration were initially found to be comprised of around 2.7 w/w % Mb/polymer. After the addition of a proteolysis step to any remove surface-associated Mb (i.e., free protein that was nonspecifically bound), the final composition of the polymersomes was found to be only 0.5 w/w % Mb/polymer, indicating that very small amounts of protein were being encapsulated within polymersomes. FIG. 6C shows the final weight percentage of Mb-to-polymer in polymersome suspensions created using thin-film rehydration at 23° C. both before and after the added proteolysis step.

Figure 6D:
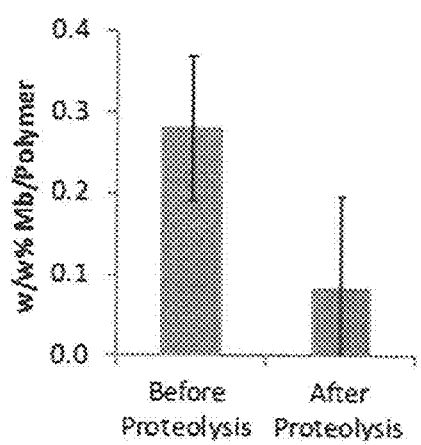

In order to improve the concentrations and the final weight percentages of myoglobin in polymersome-encapsulated myoglobin suspensions, polymersome generation at higher temperatures was again attempted utilizing thin-film rehydration at 40 and 60° C. Such tests, however, only resulted in protein denaturation and aggregation. In contrast, polymersome-encapsulated myoglobin suspensions prepared by direct hydration at 23° C. displayed good colloidal properties and the characteristic absorption spectra of intact myoglobin, yet the final loading ratio of Mb-to-polymer in these polymersome-encapsulated myoglobin suspensions was low. FIG. 6D shows the final weight percentage of Mb-to-polymer in polymersome suspensions created using direct hydration at 23° C. both before proteolysis (i.e., showing 0.3 w/w % Mb/polymer) and after proteolysis (i.e., 0.1 w/w % Mb/polymer).

Modifications to Conventional Processes

Features of both the direct hydration and thin-film rehydration techniques were iteratively evaluated in experimental conditions in order to improve polymersome-encapsulation of functional protein.

Effects of Sonication

Following the direct hydration protocol, upon addition of OB18 polymer and PEG, the sample was mixed, cooled to RT, and 10 μL of Mb solution (150 mg/mL) in PBS (10 mM, pH 7.4) was added. The sample was then further diluted with 10, 20, 50, and 100 μL of Mb solution, followed by mixing and sonication for either: A) 0 min or B) 30 min after each additional dilution step. All samples were then dialyzed for 30 h at 4° C. (molecular weight cutoff of 1000 kDa). The final Mb concentrations, weight percentages of Mb-to-polymer, and the efficiencies for Mb encapsulation in the resultant polymersome suspensions were measured by UV-Vis absorption spectroscopy, ICP-OES and compared.

In attempting encapsulation of Mb in OB18 polymersomes, and by employing the direct hydration protocol for vesicle formation, the weight ratios of Mb-to-polymer that were reproducibly obtained in the final PEM suspensions were found to again be very low (e.g., around 0.2 w/w % Mb/polymer). The encapsulation efficiency, however, could be increased by more than 30 times if the samples were sonicated for 30 min at room temperature after each dilution step (i.e., sonicating after introducing additional volumes of aqueous solution to dilute the concentration of polymer in suspension). As discussed above with respect to FIG. 3A, the relative amount of Mb in PEM suspension could be increased to around 6.0 w/w % Mb/polymer, supporting the addition of this sonication step to the original direct hydration protocol.

Effects of Blending Technique (Dissolving Polymer in Organic Solvent Vs. Addition of Heat)

The effects of utilizing an organic solvent were compared to adding heat to blend OB18 with a PEG500 homopolymer to improve polymer dissolution during the first step of the direct hydration protocol. These strategies were compared with respect to the final yield of polymersome formation and, ultimately, to the concentrations and efficiencies of protein encapsulation that could be obtained by each method. If the two polymers were first mixed by dissolution in DCM (followed by polymersome formation after organic solvent evaporation), the final weight ratio of Mb-to-polymer in PEM suspensions was around 2 w/w % Mb/polymer. In comparison, initial heating of dry OB18 and PEG500 to 95° C. for 1 h improved mixing and promoted more efficient polymersome generation, yielding a significantly higher final weight ratio of Mb-to-polymer in the final PEM suspensions (i.e., around 5 w/w % Mb/polymer), corresponding to a greater amount of encapsulated protein.

Following the direct hydration protocol, 10 mg of OB18 and 10 mg of PEG were either blended by heating at 95° C. for 1 h, or mixed by dissolution in DCM (50 μL) followed by drying under vacuum at room temperature overnight. Further encapsulation was done using the same protocol with the addition of 30 min of sonication after each dilution step. Mb concentrations in the final suspensions were determined by UV-Vis absorption spectroscopy and ICP-OES and compared.

Effects of Mb Oxidation State (i.e., Utilizing oxyMb vs. metMb for Polymersome-Encapsulation)

Myoglobin encapsulation was found to be further augmented when the starting Mb stock solution was first reduced with sodium dithionite to convert all metmyoglobin (i.e., metMb) to the oxmyoglobin (i.e., oxyMb) form. OxyMb contains a central heme group with iron in the ferrous state (i.e., Fe(II)), which improves the solubility of the protein when compared it its metMb form that contains Fe(III). This oxyMb solution was further desalted via dialysis prior to its utilization in all of the subsequent dilution steps in the direct hydration protocol, which was found to be necessary to increase the loading of Mb in PEM suspensions (i.e., the final weight ratio of Mb-to-polymer). As discussed above with respect to FIG. 3B, when oxyMb was used in the initial protocol step, PEM suspensions comprised of 6 w/w % Mb/polymer were formed, which was a statistically significant improvement over the 4 w/w % Mb/polymer obtained when metMb was utilized.

The direct hydration protocol was modified to expose the initial mixture of polymer and PEG to 1 h (instead of 20 min) of heating at 95° C. The effect of the iron oxidation state of the heme group of Mb on the efficiency of polymersome-encapsulation was studied by using oxyMb (i.e., Fe(II)Mb) vs. metMb for each dilution step. MetMb solution was prepared by dissolving lyophilized Mb in PBS; the same solution was treated with 1 wt % $Na_2S_2O_4$ to obtain the reduced Mb form (oxyMb). Mb encapsulation in polymersomes was measured by UV-Vis absorption spectroscopy and ICP-OES, and compared.

Effects of Sonication and Temperature on Mb Oxidation

More than 40% of the oxyMb that was used in the initial step for polymersome-encapsulation was found to be reoxidized to metMb within 2 h at 50° C. In contrast, only around 15% metMb was generated from the initial oxyMb solution if lower temperatures were employed for polymersome formation (e.g., heating for 2 h at 40° C.). The rate of Mb oxidation at 50° C. was also significantly higher than that at 40° C., regardless of the addition of sonication or the power that was utilized, as discussed above with respect to FIG. 3C. As such, it was determined that sonication had no effect on Mb oxidation and it was thus preferentially employed to both promote polymer mixing and to provide interfacial energy to augment polymersome formation.

The initial Mb solution (at 150 mg/mL) was reduced with $Na_2S_2O_4$ and subjected to various conditions, including heating at 40° C. (with or without sonication) or at 50° C. for 2-5 h. Mb oxidation was determined by measuring the percentages of metMb in the total polymersome-encapsulated Mb suspensions, using the cyanomethemoglobin method.

Effects of Proteolysis

Upon formation, PEM suspensions were treated with 0.4% pronase solution for up to 18 h at room temperature in order to examine the duration of time required for the complete digestion of any surface-associated (i.e., non-specifically bound) Mb. It was observed that all surface-associated Mb was digested in 2 h and that neither increasing pronase exposure time nor concentration further augmented Mb loss, thus indicating that only encapsulated Mb was retained, as discussed above with respect to FIG. 3D.

Mb was encapsulated in OB18 polymersomes using different initial solution concentrations of protein (i.e., 50, 75, and 150 mg/mL) followed by dialysis for at least 30 h at 4° C. (molecular weight cutoff of 1000 kDa). The samples were subsequently treated with 0.4 wt % pronase solution for 18 h at room temperature and again dialyzed overnight at 4° C. Mb encapsulation in polymersomes (before and after proteolysis) was measured by UV-Vis absorption spectroscopy and ICP-OES, and compared.

Improvement of Mb encapsulation efficiency (i.e., % Mb EE)

Five sets of experiments were done with various Mb-to-PBS volume ratios (i.e., "Mb:PBS") in order to establish the optimal Mb concentration to use in each subsequent dilution step in our modification of the original "direct hydration" protocol. Notably, when the Mb:PBS increased, the final w/w % Mb/polymer in the PEM suspensions also increased; but, the Mb encapsulation efficiency (i.e., % Mb EE) decreased as a result. In other words, the final Mb-to-polymer mass ratio was maximized when all dilutions steps were conducted using a maximally concentrated Mb solution (i.e., Mb:PBS=190:0 and 150 mg/mL oxyMb). As discussed above with respect to FIG. 3E, the % Mb EE was largest when the Mb:PBS was minimal (i.e., 10:180). As the amount of protein in the final polymersome suspension is ultimately the metric that must be optimized for therapeutic administration (in order to minimize the amount of associated carrier polymer that is introduced to a subject), it was determined that a pure Mb solution (150 mg oxyMb/mL) would be used for each dilution step in the ultimate encapsulation protocol, maximizing the final w/w % Mb/polymer in PEM suspensions.

Following the basic direct hydration protocol, 10 mg polymer and 10 mg of PEG were initially heated in 1.5 mL microcentrifuge tubes for 1 h at 95° C. and subsequently cooled to RT. The mixtures were then diluted by adding 10, 10, 20, 50, and 100 μL of diluents. Two different solutions were used and compared for each of the 5 dilution steps: PBS and/or Mb suspensions (i.e., 150 mg/mL Mb in PBS). The final (v/v) ratio of Mb to PBS (i.e., "Mb:PBS") used as diluents in steps 1, 2, 3, 4, and 5 were 10:180, 20:170, 40:150, 90:100, and 190:0, respectively. The samples were then proteolyzed using 0.4 wt % pronase and again dialyzed overnight at 4° C. (molecular weight cutoff of 1000 kDa). Mb encapsulation was measured using UV-Vis absorption spectroscopy. The Mb encapsulation efficiencies were calculated using Equation 4:

$$Mb \text{ Encapsulation Efficiency} = \left[1 - \frac{v_1 c_1 - v_2 c_2}{v_1 c_1}\right] \times 100, \quad \text{(Eq. 4)}$$

Where $v_1$=Initial volume of the unencapsulated Mb (mL), $c_1$=Initial concentration of unencapsulated Mb (mg/mL), $v_2$=volume of polymersome-encapsulated Mb obtained after dialysis and proteolysis (mL), and $c_2$=concentration of encapsulated Mb obtained after dialysis and proteolysis (mg/mL)

Using Progressive Saturation to Generate Polymersome-Encapsulated Protein Suspensions.

By incorporating each of the steps in the various embodiments, a progressive saturation technique was established, represented in FIG. 7A, which vastly improved upon the results of the original direct hydration protocol discussed above with respect to FIG. 5C. Using the progressive saturation protocol, the final content of Mb in OB18-based PEM suspensions was found to be 6.1 and 3.2 w/w % Mb/polymer before and after proteolysis, respectively. Quantification of the iron content (numbers of intact heme groups) in each of the polymersome suspensions by ICP-OES corroborated UV-Vis measurements of protein concentration. As shown in FIG. 7B, the final loading ratios of Mb in the polymersomes were found to be 7.9 and 5.1 w/w % Mb/polymer before and after proteolysis, respectively. As shown in FIG. 7C, the percentage of metMb (with respect to the total Mb content in these suspensions) was determined by UV-Vis absorbance spectroscopy and found to be around 8% and 6% in non-proteolyzed (PEM-SE) and proteolyzed (PEM-E) samples, respectively. FIG. 7D is a table of the measured properties (i.e., results) for the OB18-based PEM suspensions, as discussed with respect to FIGS. 7B and 7C.

Stability of Polymersome-Encapsulated Protein Suspensions

OB18-encapsulated Mb suspensions were prepared using the optimized progressive saturation technique. The samples were stored at 4, 23, and 37° C. for 3 weeks. At predetermined time points, the samples were diluted with PBS and the mean particle size and distributions were determined by DLS.

Equilibrium Binding of Oxygen in Polymersome-Encapsulated Mb Suspensions

The equilibrium binding and dissociation curves for oxygen in suspensions of free and polymersome-encapsulated Mb were obtained at 37° C. using a Hemox™-Analyzer. Samples were allowed to saturate to a $pO_2$ of 147 mmHg (using compressed air) and then deoxygenated (using a compressed nitrogen stream). The absorbance of oxygenated and deoxygenated free and polymersome-encapsulated Mb suspensions was recorded as a function of $pO_2$ via dual wavelength spectroscopy. Oxygen equilibrium curves were fit to a four-parameter ($A_0$, $A_\infty$, $P_{50}$, n) Hill model (Equation 5). In this model, $A_0$ and $A_\infty$ represent the absorbance at 0 mmHg and at 147 mmHg, respectively. The $pO_2$ represents the partial pressure of oxygen; and, $P_{50}$ represents the partial pressure of $O_2$ where the sample is 50% saturated with oxygen. Lastly, n represents the cooperativity coefficient for the sample.

$$Y = \frac{\text{Abs} - A_0}{A_\infty - A_0} = \frac{pO_2^n}{pO_2^n + P_{50}^n}. \quad \text{(Eq. 5)}$$

FIG. 7E shows the $P_{50}$ values (in mmHg) obtained for a free myoglobin (Mb) sample, a polymersome-encapsulated myoglobin sample prior to proteolysis (PEM-SE) that was prepared using the progressive saturation technique, and a polymersome-encapsulated myoglobin sample after pronase treatment (PEM-E) that was prepared using the progressive saturation technique.

Characterization of the Final PEM Suspensions

Figure 8A:
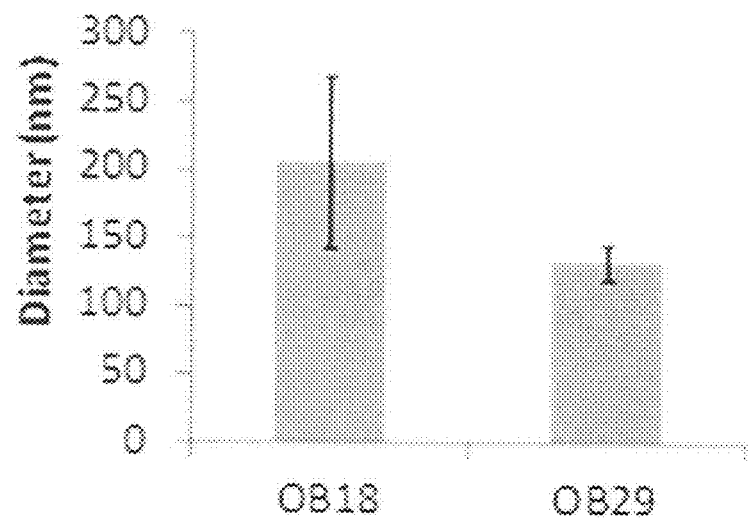
FIG. 8A is a graph showing results from encapsulation of myoglobin into polymersomes formed from two particular PEO-b-PBD formulations using the progressive saturation technique of the various embodiments.
Figure 8B:
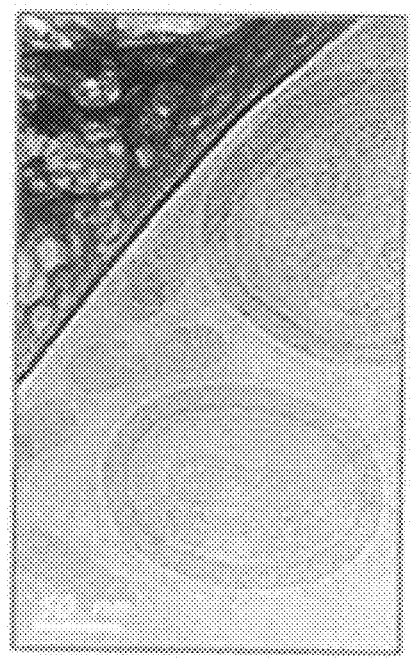
FIGS. 8B and 8C are cryo-TEM images of vesicles in polymersome-encapsulated myoglobin suspensions formed from each of the particular PEO-b-PBD formulations using the progressive saturation technique of the various embodiments.
Figure 8C:
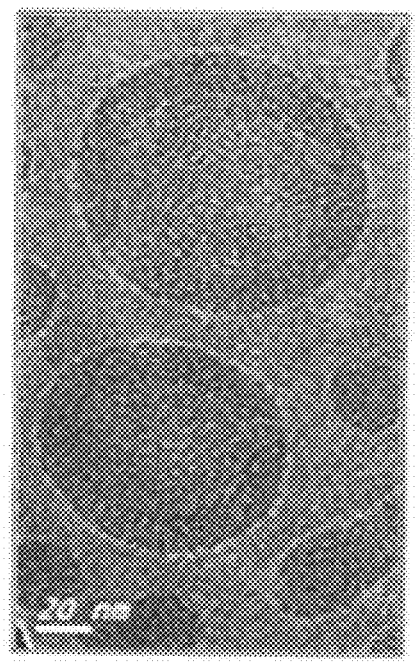
Figure 8D:
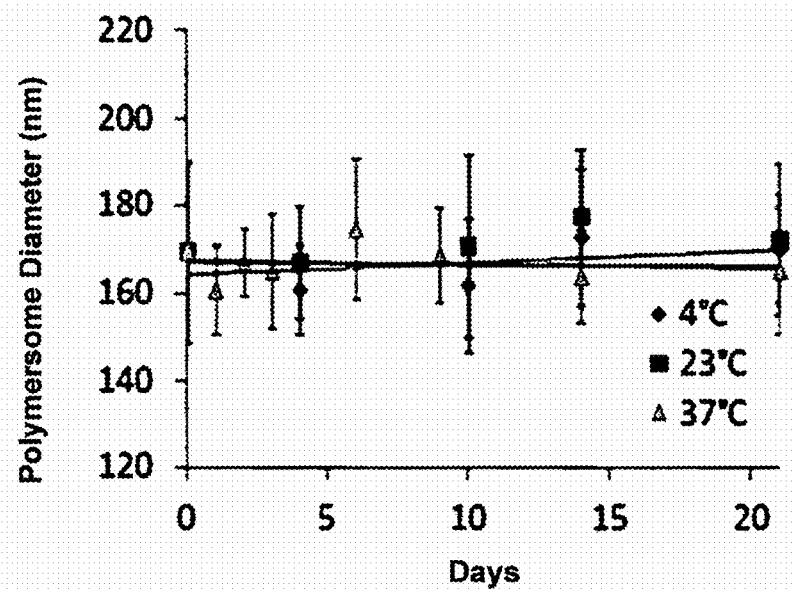
FIG. 8D is a graph showing the average hydrodynamic diameters of a polymersome-encapsulated myoglobin suspension formed from a particular PEO-b-PBD formulation using the progressive saturation technique of the various embodiments.
Figure 8E:
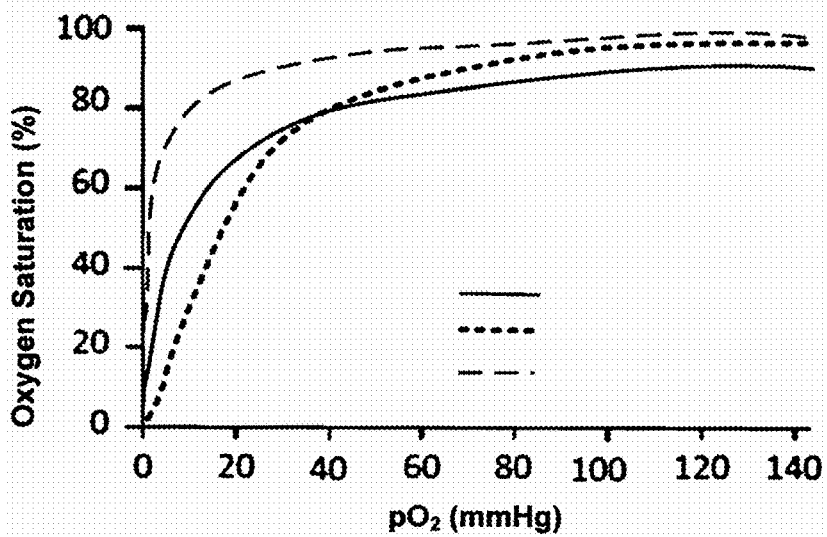
FIG. 8E is a graph showing the oxygen equilibrium curves for free oxymyoglobin and oxygenated polymersome-encapsulated myoglobin suspension formed from a particular PEO-b-PBD formulation using the progressive saturation technique of the various embodiments.

The size distributions of the final OB18- and OB29-based PEM suspensions were measured by both DLS and cryo-TEM. FIG. 8A provides the average hydrodynamic diameter of particles in OB18-based and OB29-based PEM suspensions prepared using progressive saturation, as assessed by DLS. Cryo-TEM images of vesicles in OB18-based and OB29-based PEM suspensions are shown in FIGS. 8B and 8C, respectively. These results confirmed a mean particle diameter of approximately 200 nm for OB18 polymersomes, and 130 nm for OB29 polymersomes. The stability of the OB18-based PEM suspensions were further examined over three weeks and at various temperatures, with the polymersomes, demonstrating no aggregation based on the consistent particle numbers and stable size distributions in suspension. FIG. 8D shows the average hydrodynamic diameters of particles, as determined by DLS, in OB18-based PEM suspensions that were prepared by progressive saturation at various temperatures (i.e., 4° C., 23° C., and 37° C.) as a function of time. Finally, the functional status of encapsulated Mb in the PEM suspensions (i.e., retention of Mb's ability to bind and release oxygen) was verified by dual wavelength spectroscopy. FIG. 8E shows oxygen equilibrium curves for free oxyMb and oxygenated OB18-based PEM suspensions. Error bars denote standard deviation of the mean. n≥3 experimental replicates per condition. The oxygen equilibrium curves, $P_{50}$ (i.e., the partial pressure of $O_2$ where the Mb is 50% saturated with oxygen) of PEM were very similar to those of free Mb in solution.

Polymersome-Encapsulation Using Block Copolymers and Proteins of Varying Molecular Weight The generalizability of the progressive saturation technique was tested using proteins of various sizes: i.e., Mb (17 kDa), hemoglobin (Hb; 64 kDa), bovine serum albumin (BSA; 66 kDa), immunoglobulin G (IgG: 150 kDa), catalase (250 kDa), fibrinogen (340 kDa), and apoferritin (450 kDa); each protein was dissolved in PBS (10 mM, pH 7.4) at its maximal solubility, corresponding to final suspension concentrations of 150, 150, 40, 20, 50, 50, and 25 mg/mL, respectively. The progressive saturation protocol was followed to encapsulate these proteins in OB29 polymersomes. Free proteins were separated by dialysis for at least 30 h at 4° C. (molecular weight cutoff of 1000 kDa). Surface associated protein was removed by proteolysis via treatment with 0.4 wt % pronase solution followed by overnight dialysis at 4° C. (molecular weight cutoff of 1000 kDa). Protein encapsulation (before and after proteolysis) in polymersome suspensions was quantified via the micro-BCA assay, utilizing UV-Vis spectrophotometry and by following the manufacturer's protocols (Pierce Biotechnology, Inc; Rockford, Ill., USA). The final concentrations of protein were divided by those of polymer and expressed as the final weight ratios of protein-to-polymer that comprised the polymersomes in suspension (e.g., w/w % Mb/polymer).

Statistical Analysis

Data are presented as the mean±the standard deviation of the mean (SD). A minimum of three experimental replicates was used for each condition. One-way analysis of variance (ANOVA) was conducted using GraphPad software (San Diego, USA). A p value of <0.05 was considered statistically significant.

What is claimed is:

1. A composition, comprising:
a suspension of a polymersome-encapsulated functional protein, wherein the suspension is prepared by:
thermally blending a quantity of an amphiphilic diblock copolymer with a quantity of polyethylene glycol (PEG), wherein the amphiphilic diblock copolymer comprises poly(ethylene oxide)-block-poly(butadiene) (PEO-b-PBD);
adding an aliquot of a solution of the functional protein to a sample containing the PEG/polymer formulation, wherein the solution of the functional protein comprises oxymyoglobin or metmyoglobin in phosphate buffered saline (PBS); and
performing at least one dilution step such that polymersomes that are generated are progressively saturated with the functional protein.

2. The composition of claim 1, wherein preparing the suspension of a polymersome-encapsulated functional protein comprises:
thermally blending a quantity of an amphiphilic diblock copolymer with a quantity of polyethylene glycol (PEG) for at least 30 minutes, wherein the thermal blending is performed at 90-100° C.;
mixing and cooling a resulting PEG/polymer formulation to room temperature;
adding an aliquot of a solution of the functional protein to a sample containing the PEG/polymer formulation,
wherein a ratio of the added aliquot to the PEG/polymer formulation is between around 0.5:1 and around 1.5:1 by volume; and
performing at least three dilution steps such that polymersomes that are generated are progressively saturated with the functional protein, wherein each dilution step comprises:
adding to the sample an additional amount of the solution of the functional protein;
mixing a resulting dispersion of the functional protein in the PEG/polymer formulation; and
sonicating the resulting dispersion for at least 30 minutes.

3. The composition of claim 2, wherein performing the at least three dilution steps comprises performing a first, a second, and a third dilution step in a serial fashion, wherein:
adding the additional amount of the solution in the first step comprises adding a first amount of the solution of the functional protein such that a ratio of the first amount to the PEG/polymer formulation is around 1:1 by volume;
adding the additional amount of the solution in the second step comprises adding a second amount of the solution of the functional protein such that a ratio of the second amount to the PEG/polymer formulation is around 2:1 by volume; and
adding the additional amount of the solution in the third step comprises adding a third amount of the solution of the functional protein such that a ratio of the third amount to the PEG/polymer formulation is around 5:1 by volume.

4. The composition of claim 3, wherein performing the at least three dilution steps further comprises performing a fourth dilution step, wherein adding the additional amount of the solution in the fourth step comprises adding a fourth amount of the solution of the functional protein such that a ratio of the fourth amount to the PEG/polymer formulation is around 5:1 by volume.

5. The composition of claim 4, further comprising removing surface-associated protein from polymersomes in the suspension of the polymersome-encapsulated functional protein, after the at least three dilution steps using proteolysis.

6. The composition of claim 5, wherein using proteolysis comprises:
treating the PEG/polymer/protein sample with a 0.4 wt % pronase solution for at least 18 hours at room temperature; and
allowing dialysis of the mixed PEG/polymer/protein sample at 4° C. for at least twelve hours.

7. The composition of claim 1, wherein the solution of the functional protein comprises a 150 mg/mL solution of oxymyoglobin in phosphate buffered saline (PBS).

8. The composition of claim 7, further comprising preparing the solution of the functional protein by:
combining a solution of 150 mg/mL metmyoglobin (metMb) in phosphate buffered saline with sufficient amount of 1 wt % sodium dithionite ($Na_2S_2O_4$) to reduce to the metMb to oxymyoglobin (oxyMb).

9. The composition of claim 1, wherein thermally blending the quantity of the block copolymer with the quantity of the low molecular weight PEG for at least 30 minutes comprises thermally blending 5-15 mg of poly(ethylene oxide)-block-poly(butadiene) (PEO-b-PBD) with 5-15 mg of 500 kDa PEG (PEG500) for at least one hour.

10. The composition of claim 1, wherein:
thermally blending the amphiphilic diblock copolymer with the low molecular weight PEG for at least 30 minutes comprises thermally blending 10 mg of poly(ethylene oxide)-block-poly(butadiene) (PEO-b-PBD) with 10 mg of 500 kDa PEG (PEG500) for one hour; and adding the aliquot of the solution of the functional protein comprises adding 10 μL of an oxymyoglobin solution to the sample of the PEG/polymer formulation.

11. The composition of claim 1, wherein the thermal blending is performed at around 95° C.

* * * * *